United States Patent
Connolly et al.

(10) Patent No.: US 11,672,676 B2
(45) Date of Patent: Jun. 13, 2023

(54) SYSTEM AND METHOD FOR NONINVASIVE IDENTIFICATION OF COGNITIVE AND BEHAVIORAL GOALS

(71) Applicant: Teledyne Scientific & Imaging, LLC, Thousand Oaks, CA (US)

(72) Inventors: Patrick M. Connolly, Cary, NC (US); Stephen Simons, Raleigh, NC (US); Karen Zachery, Raleigh, NC (US); Barry Ahrens, Fayetteville, NC (US); Mario Aguilar-Simon, Chapel Hill, NC (US); William D. Reynolds, Jr., Raleigh, NC (US); David Krnavek, Durham, NC (US)

(73) Assignee: TELEDYNE SCIENTIFIC & IMAGING, LLC, Thousand Oaks, CA (US)

( * ) Notice: Subject to any disclaimer, the term of this patent is extended or adjusted under 35 U.S.C. 154(b) by 193 days.

(21) Appl. No.: 17/141,920

(22) Filed: Jan. 5, 2021

(65) Prior Publication Data

US 2021/0205104 A1 Jul. 8, 2021

Related U.S. Application Data

(63) Continuation of application No. 15/678,848, filed on Aug. 16, 2017, now Pat. No. 10,945,864.

(Continued)

(51) Int. Cl.
*A61F 2/72* (2006.01)
*G06F 3/01* (2006.01)
(Continued)

(52) U.S. Cl.
CPC .............. *A61F 2/72* (2013.01); *A61B 3/113* (2013.01); *A61B 5/11* (2013.01); *A61B 5/16* (2013.01);
(Continued)

(58) Field of Classification Search
CPC ... A61B 3/113; A61B 5/7264; A61B 5/04009; A61B 5/04017; A61B 5/04842;
(Continued)

(56) References Cited

U.S. PATENT DOCUMENTS 7,299,088 B1  11/2007  Thakor
7,580,742 B2  8/2009  Tan et al.
(Continued)

FOREIGN PATENT DOCUMENTS

WO  WO-2006122349 A1 * 11/2006 ......... A61B 5/04845
WO  WO 2012/141714 A1  10/2012
WO  WO 2014/092494 A1  6/2014

OTHER PUBLICATIONS

Das et al., "Multiple Feature Extraction of Electroencephalograph Signal for Motor Imagery Classification through Bispectral Analysis", Procedia Computer Science, vol. 84, 2016, pp. 192-197.

(Continued)

*Primary Examiner* — Christie L Bahena
(74) *Attorney, Agent, or Firm* — K&L Gates LLP

(57) ABSTRACT

A brain machine interface system for use with an electroencephalogram to identify a behavioral intent of a person is disclosed. The system includes an electroencephalogram configured to sense electromagnetic signals generated by a brain of a person. The electromagnetic signals include a time component and a frequency component. A monitor monitors a response of the person to a stimulus and a characteristic of the stimulus. A synchronization module synchronizes the sensed electromagnetic signals with the response and the characteristic to determine a set of electromagnetic signals corresponding to the monitored response and the characteristic. A processor processes the set of electromagnetic signals and extracts feature vectors. The feature vectors define a class of behavioral intent. The processor determines the behavioral intent of the person based on the feature vectors. A brain machine interface and a method for identifying a behavioral intent of a person is also disclosed.

15 Claims, 21 Drawing Sheets

Related U.S. Application Data

(60) Provisional application No. 62/420,950, filed on Nov. 11, 2016, provisional application No. 62/376,361, filed on Aug. 17, 2016.

(51) Int. Cl.

| | |
|---|---|
| *A61B 5/16* | (2006.01) |
| *A61B 5/38* | (2021.01) |
| *A61B 5/246* | (2021.01) |
| *A61B 5/316* | (2021.01) |
| *A61B 5/374* | (2021.01) |
| *A61B 5/378* | (2021.01) |
| *A61B 3/113* | (2006.01) |
| *A61B 5/11* | (2006.01) |
| *A61B 5/00* | (2006.01) |
| *G06F 3/04842* | (2022.01) |

(52) U.S. Cl.
CPC .............. *A61B 5/246* (2021.01); *A61B 5/316* (2021.01); *A61B 5/374* (2021.01); *A61B 5/378* (2021.01); *A61B 5/38* (2021.01); *A61B 5/7264* (2013.01); *G06F 3/013* (2013.01); *G06F 3/015* (2013.01); *G06F 3/04842* (2013.01)

(58) Field of Classification Search
CPC ......... A61B 5/04845; A61B 5/11; A61B 5/16; G06F 3/015
See application file for complete search history.

(56) References Cited

U.S. PATENT DOCUMENTS

| | | |
|---|---|---|
| 10,064,578 B2 | 9/2018 | Garcia Molina et al. |
| 10,945,864 B2 | 3/2021 | Connolly et al. |
| 2010/0100001 A1 | 4/2010 | Aguilar et al. |
| 2014/0277582 A1 | 9/2014 | Leuthardt et al. |

OTHER PUBLICATIONS

Shahid et al., "Bispectrum-based feature extraction technique for devising a practical brain-computer interface", Mar. 24, 2011, IOP Publishing Ltd., Journal of Neural Engineering, vol. 8, No. 2, 25014, pp. 1-12.

Chua et al., "Application of higher order statistics/spectra in biomedical signals: A Review", Medical Engineering and Physics, vol. 32, No. 7, Sep. 2010, pp. 679-689.

Communication pursuant to Article 94(3) from the Examining Division for European Patent Application No. 17758017.2, May 19, 2022, 7 pages.

International Search Report and Written Opinion for International Application No. PCT/US2017/047349 dated Nov. 29, 2017.

International Preliminary Report on Patentability for International Application No. PCT/US2017/047349 dated Feb. 19, 2019.

Haufe et al., "EEG potentials predict upcoming emergency brakings during simulated driving", Journal of Neural Engineering, IOP Publishing, 2011, vol. 8, pp. 1-11.

Jang et ai., "Recognition of Human's implicit Intention Based on an Eyeball Movement Pattern Analysis", ICONIP, Springer-Verlag Berlin Heidelberg, Nov. 13, 2011, Part I, pp. 138-145.

Choi et al., "Enhanced Perception of User Intention by Combining EEG and Gaze-Tracking for Brain-Computer Interfaces (BCIs)", Sensors, vol. 13, Mar. 13, 2013, pp. 3454-3472.

Lew, Eileen, "Detection of self-paced reaching movement intention from EEG signals", Frontiers in Neuroengineering, vol. 5, Jul. 2012, Article 13, pp. 1-17.

Kim et al., "Detection of braking intention in diverse situations during simulated driving based on EEG feature combination", Journal of Neural Engineering, vol. 12, 2015, 12 pages.

Parra et al., "Single-trial detection in EEG and MEG: Keeping it linear", Neurocomputing. vols. 52-54, 2003, pp. 177-183.

Parra et al., "Recipes for the linear analysis of EEG", NeuroImage, vol. 28, 2005, pp. 326-341.

Royer et al., "Goal selection vs. Process Control in a Brain-Computer Interface based on Sensorimotor Rhythms", Journal of Neural Engineering, vol. 6, No. 1, 2009, 25 pages.

Royer et al., "Goal Selection vs. Process Control while Learning to Use a Brain-Computer Interface", Journal of Neural Engineering, 2011, vol. 8, No. 3, 20 pages.

Johansen et al., "Development and Clinical Application of Electroencephalographic Bispectrum Monitoring", Anesthesiology, vol. 93, No. 5, Nov. 2000, pp. 1336-1344.

Kelley et al., Anesthesia Awareness and the Bispectral Index, The New England Journal of Medicine, vol. 359, No. 4, Jul. 24, 2008, pp. 427-431.

Williams, Adam, Flying Drone Controlled with Mind Power, New Atlas, Sep. 1, 2012, 9 pages.https://newatlas.com/ar-drone-quadrocopter-thought-control/23960.

\* cited by examiner

SYSTEM AND METHOD FOR NONINVASIVE IDENTIFICATION OF COGNITIVE AND BEHAVIORAL GOALS

CROSS-REFERENCE TO RELATED APPLICATIONS

This application is a continuation application filed under 35. U.S.C. § 120 of U.S. patent application Ser. No. 15/678, 848 entitled "SYSTEM AND METHOD FOR NONINVASIVE IDENTIFICATION OF COGNITIVE AND BEHAVIORAL GOALS" filed on Aug. 16, 2017, which, in turn, claims the benefit of U.S. Provisional Application No. 62/376,361, filed Aug. 17, 2016, and claims the benefit of U.S. Provisional Application No. 62/420,950, filed Nov. 11, 2016, each of which is herein incorporated by reference in its entirety.

STATEMENT OF GOVERNMENTAL INTEREST

This invention was made with U.S. Government support under Army contract number W911NF-09-D-0001, subcontract number KK1323. The U.S. Government has certain rights in the invention.

FIELD OF TECHNOLOGY

This disclosure is directed generally to a system and method for using an electroencephalogram (EEG) or another brain sensing method to detect the cognitive or behavioral goals of a person in order to improve the quality of brain machine interfaces (BMIs). Other brain sensing methods may include functional near-infrared spectroscopy (fNIRS), magnetoencephalography (MEG), and functional magnetic resonance imaging (fMRI).

BACKGROUND

EEG senses electrical activity in the brain using electrodes comprising small, flat metal discs that are attached to the scalp of a person. The electrodes may be mounted on an elastic cap. EEG can measure the electric field generated by a group of neurons generating electrical impulses in synchronization. EEG also can provide information regarding the timing of electrical activity, such as which areas of the brain are activated at a particular time. Often, a classifier is used to analyze the EEG, fNIRS, MEG or fMRI signals to infer the existence of certain brain states. For example, U.S. Pub. No. 2007/0185697 entitled "Using Electroencephalograph Signals for Task Classification and Activity Recognition" describes a trial-averaged spatial classifier for discriminating operator performed tasks for EEG signals. Recent advances in adaptive signal processing have demonstrated significant single trial detection capability by integrating EEG data spatially across multiple channels of high density EEG sensors (L. Parra et al, "Single Trial Detection in EEG and MEG: Keeping it Linear", Neurocomputing, vol. 52-54, June 2003, pp. 177-183, 2003 and L. Parra et al, "Recipes for the Linear Analysis of EEG", NeuroImage, 28 (2005), pp. 242-353)). The linear (LDA) classifier provides a weighted sum of all electrodes over a predefined temporal window as a new composite signal that serves as a discriminating component between responses to target versus distractor stimuli. Head orientation and eye activity provide a way to determine whether the user is likely to perceive information presented on the screen.

Related art for decoding motor intent in prosthetic control includes patent application publication WO 2012141714 A1, titled Multi-Modal Neural Interfacing For Prosthetic Devices, the disclosure of which is incorporated herein by reference. Other related art includes Royer, Audrey S. and Bin He, "Goal Selection Versus Process Control In A Brain-Computer Interface Based On Sensorimotor Rhythms," Journal Of Neural Engineering, 6 (2009) 016005 (12 pp) and, Royer, Audrey S., Minn L. Rose, and Bin He, "Goal Selection Versus Process Control While Learning To Use A Brain-Computer Interface," Journal Of Neural Engineering, 8 (2011) 036012 (12 pp), each of which is incorporated herein by reference in its entirety. The related art does not disclose the detection of goal related signals using EEG. Likewise, Royer and He (2009, 2011) do not disclose goal directed brain-computer interfaces (BCIs) that directly determine behavioral goals using EEG signals. Instead, Royer and He describe implementing a goal selection strategy for direct motor control rather than goal state classification for direct behavioral intent detection. Specifically, the goal selection strategy may be for determining whether a BCI user intends to move a prosthetic arm left or right. Therefore, the goal selection strategy comprises using the BCIs to control low-level motor commands that do not directly represent high-level behavioral goals as understood in the context of the present disclosure. Given these limitations in the present technology, it may be useful to devise a system and method for using EEG as a methodology for practical BMIs to detect the cognitive or behavioral goals of a person. Cognitive or behavioral goals may refer to the behavioral intent of a person, in contrast to discrete low level direct control actions such as moving a prosthetic arm.

The present disclosure provides a system and method for using EEG or other brain sensing methods in an improved BMI to determine the intent of a user of the BMI. Determining the intent may refer to, for example, extracting cognitive or behavioral goal related intent directly from the brain of a user. In one non-limiting example, the user is equipped with an EEG headset, an eye scanner, and auditory feedback device. In one aspect, the user is positioned at a simulated Army vehicle crew station. The disclosed system and method improves conventional BMIs because conventional BMIs utilize signals encoding simple information such as binary labels (e.g., target vs. non-target). In addition, conventional BMIs do not directly decode end goals from brain signals but instead incorporate such signals in a non-intuitive and complex mapping scheme to determine an end goal of the user. In contrast, the improved BMI of the present disclosure may directly determine the intent of the user. Decoding signals to determine the cognitive or behavioral goals of users by the improved BMI may be applied to a broad set of applications such as task automation, prosthetic control simplification, human computer interaction, and human augmentation. Human augmentation may refer to, for example, human control of external devices or to enhanced abilities such as providing direct textual input. In such applications, a chain of decisions of the user can be decoded and used to interact with computers in a novel manner.

The system and method according to the present disclosure provides efficient interaction between the brain of a person and a machine. For example, the brain may interact with a machine located, for example, in a cockpit, vehicle console or at an Army vehicle crew station. Conventional approaches for BMIs have non-intuitive interfaces and/or have significantly reduced available bandwidth in comparison to a normal manual interaction approach. A manual interaction may refer to a manual operation such as, for example, the person performing a touch operation on a touch interface of the machine to perform a function. In contrast, the disclosed system will enable a user to communicate intended actions to automated processes without a manual operation. Therefore, the disclosed system will improve the efficiency and effectiveness of interactions between the person and the machine, especially in multi-modal environments.

The present disclosure provides a system and method for using EEG or another suitable brain sensing method to detect the cognitive or behavioral goals of a person in order to improve the quality of BMIs. Cognitive or behavioral goals may refer to the behavioral intent of a person. The quality of the BMIs are improved based on the noninvasive and direct intent decoding aspect of the BMIs. The disclosed improved BMIs directly determine behavioral intent rather than based on proxy signals used by many conventional BMIs. Proxy signals may be, for example, steady-state visual evoked potentials (SSVEPs) that may be generated because of artificial physical stimulation by a sensory stimulus designed to evoke a particular response. In contrast to conventional BMIs that rely on proxy signals, the disclosed BMIs directly decode the innately generated intent signals of a user in response to unmanipulated stimuli. In addition, the disclosed improved BMIs detect behavioral intent with respect to both visual and auditory inputs. The disclosed improved BMIs are designed for use at a vehicle crew station.

SUMMARY

In one aspect, the present disclosure provides a system that uses EEG and eye tracking feedback to extract intended behavioral goals from a user of the BMI as they relate to responses to stimuli encountered during his or her interaction with a real or simulated environment, such as, for example, an Army vehicle crew station. The system is configured to decode the context of the intended goal, such as, a response to visual or auditory events. The system is also configured to decode the relevant behavioral goal given the decoded context. One specific application enables users to automatically categorize vehicles as "Threat," "Friendly," or "Neutral." These intended responses (i.e. intended categorization) lead to a target hand-off and/or automated targeting of a threat vehicle, or appropriate automatic labeling and updating of a graphical user interface. When the system decodes behavioral goals in response to auditory cues, the system enables the users to categorize the stimuli as "Near," "Mid-Range," or "Far." These intended responses can, for example, lead to the following actions: alerting the gunner, cueing an unmanned aerial vehicle (UAV) to observe, or cueing another squad to the potential threat, respectively.

In one aspect, the present disclosure provides a brain machine interface system for use with EEG to identify a behavioral intent of a person. The system comprises EEG configured to sense electromagnetic signals generated by a brain of a person, wherein the electromagnetic signals comprise a time component and a frequency component; a monitor configured to monitor a response of the person to a stimulus and a characteristic of the stimulus; a synchronization module configured to synchronize the sensed electromagnetic signals with the response and the characteristic to determine a set of electromagnetic signals corresponding to the monitored response of the person and the characteristic; a processor configured to process the set of electromagnetic signals and to extract feature vectors, wherein each of the feature vectors define a class of behavioral intent; and wherein the processor is further configured to determine the behavioral intent of the person based on the feature vectors.

In another aspect, the present disclosure provides a brain machine interface comprising an EEG configured to sense electromagnetic signals generated by a brain of a person, wherein the electromagnetic signals comprise a time component and a frequency component; an eye tracking monitor configured to determine that the person is looking at a first stimulus; an auditory monitor configured to determine the presence of a second stimulus based on an auditory volume corresponding to the second stimulus; a processor configured to segment the electromagnetic signals into a first segment and a second segment, wherein the first segment corresponds to the first stimulus and the second segment corresponds to the second stimulus; wherein the processor is configured to process the first segment and the second segment and wherein the processor is configured to extract a first set of feature vectors from the first segment and a second set of feature vectors from the second segment, wherein each of the first set and the second set of feature vectors define a class of behavioral intent; and determine a first behavioral intent based on the first set of feature vectors and a second behavioral intent based on the second set of feature vectors.

In yet another aspect, the present disclosure provides a method for identifying a behavioral goal of a person. The method comprises sensing, by an EEG attached to a person, electromagnetic signals generated by a brain of the person, wherein the electromagnetic signals comprise a time component and a frequency component; detecting, by a monitor, an eye movement of the person and a volume of an auditory stimulus; extracting, by a processor, a first set of feature vectors corresponding to a visual stimulus and a second set of feature vectors corresponding to the auditory stimulus, wherein each of the feature vectors define a class of behavioral intent; and determining, by the processor, a behavioral intent of the person based on the first set of feature vectors and the second set of feature vectors.

In addition to the foregoing, various other method and/or system and/or program product aspects are set forth and described in the teachings such as text (e.g., claims and/or detailed description) and/or drawings of the present disclosure.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

In one or more various aspects, related systems include but are not limited to circuitry and/or programming for effecting herein-referenced method aspects; the circuitry and/or programming can be virtually any combination of hardware, software, and/or firmware configured to effect the herein-referenced method aspects depending upon the design choices of the system designer. In addition to the foregoing, various other method and/or system aspects are set forth and described in the teachings such as text (e.g., claims and/or detailed description) and/or drawings of the present disclosure.

The foregoing summary is illustrative only and is not intended to be in any way limiting. In addition to the illustrative aspects and features described above, further aspects and features will become apparent by reference to the drawings and the following detailed description.

BRIEF DESCRIPTION OF THE DRAWINGS

The novel features of the aspects described herein are set forth with particularity in the appended claims. The aspects, however, both as to organization and methods of operation may be better understood by reference to the following description, taken in conjunction with the accompanying drawings as follows.

DETAILED DESCRIPTION

Figure 1:
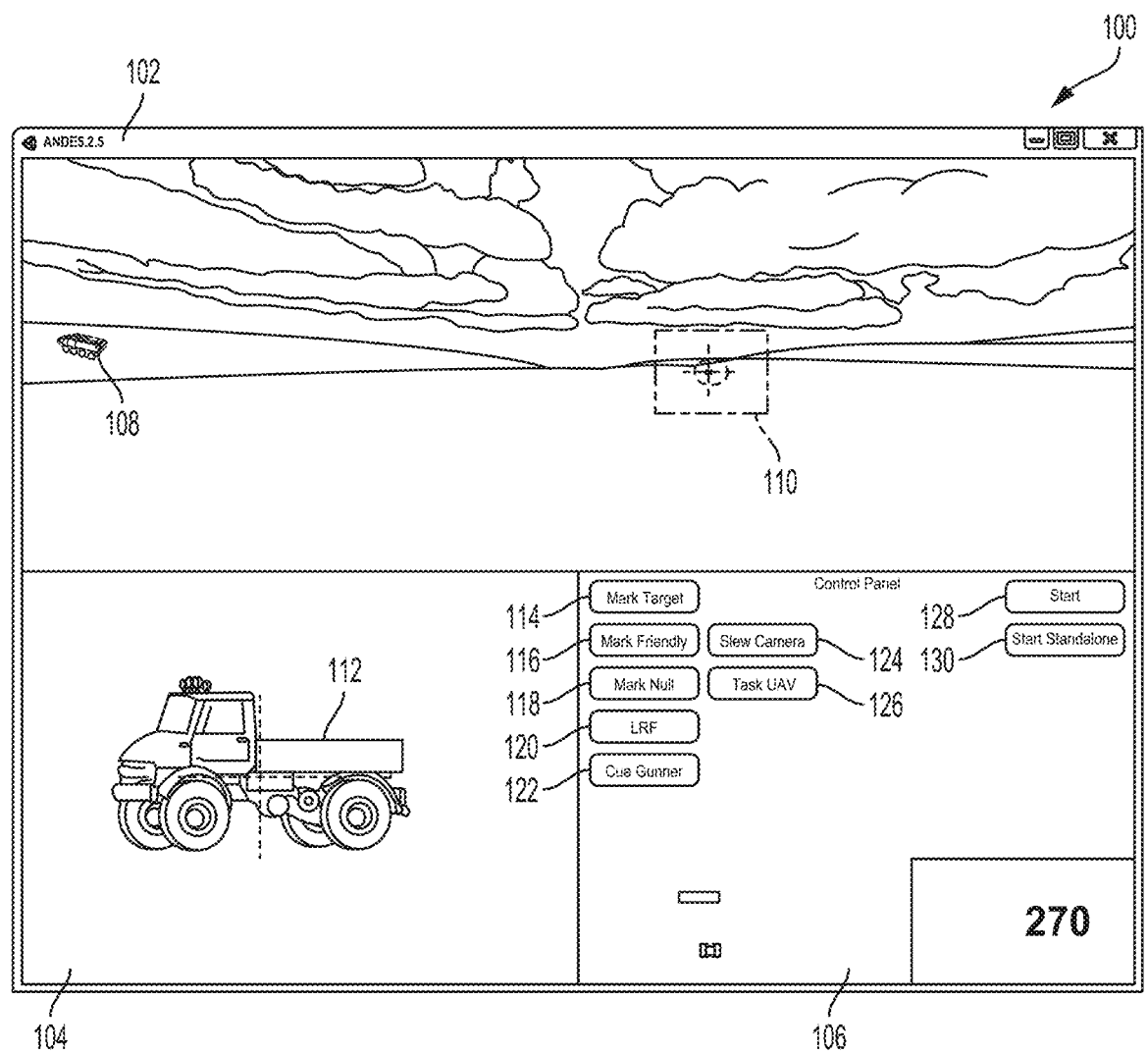
FIG. 1 depicts a simulated crew station interface for use with a brain machine interface (BMI), according to one aspect of the present disclosure.

In the following detailed description, reference is made to the accompanying drawings, which form a part hereof. In the drawings, similar symbols and reference characters typically identify similar components throughout the several views, unless context dictates otherwise. The illustrative aspects described in the detailed description, drawings, and claims are not meant to be limiting. Other aspects may be utilized, and other changes may be made, without departing from the scope of the subject matter presented here.

Before explaining the various aspects of the system and method for noninvasive identification of cognitive and behavioral goals in detail, it should be noted that the various aspects disclosed herein are not limited in their application or use to the details of construction and arrangement of parts illustrated in the accompanying drawings and description. Rather, the disclosed aspects may be positioned or incorporated in other aspects, variations and modifications thereof, and may be practiced or carried out in various ways. Accordingly, aspects of the system and method for noninvasive identification of cognitive and behavioral goals disclosed herein are illustrative in nature and are not meant to limit the scope or application thereof. Furthermore, unless otherwise indicated, the terms and expressions employed herein have been chosen for the purpose of describing the aspects for the convenience of the reader and are not to limit the scope thereof. In addition, it should be understood that any one or more of the disclosed aspects, expressions of aspects, and/or examples thereof, can be combined with any one or more of the other disclosed aspects, expressions of aspects, and/or examples thereof, without limitation.

The present disclosure is related generally to EEG or other brain sensing methods to detect a person's cognitive or behavioral goals in order to improve the quality of BMIs. In one aspect, the present disclosure is directed to improving techniques for directly extracting goal related intent from the brain of an individual.

In one aspect, the present disclosure provides a system and method for using EEG or other brain sensing methods to detect a person's cognitive or behavioral goals in order to improve the quality of BMIs. In one specific application, the present disclosure provides a system and method to determine the intent of a user located at a simulated Army vehicle crew station. For example, BMIs utilize signals to encode simple information (e.g., binary object labels) and non-intuitive and complex mapping schemes. The present disclosure provides a system and method to decode natural brain states across multiple modalities. Decoding cognitive or behavioral goals results in a broad set of applications where the chain of decisions by the user can be decoded and used in interacting with computers.

In various aspects, the present disclosure provides an intent decoding system and method. For example, the present disclosure provides an application of the intent decoding system and method to an army crew station environment. The disclosed system and method uses EEGs and/or other brain-sensing modalities that provide suitable time resolution and frequency resolution to detect desired features. The disclosed system and method detect an intended response of an individual. In one aspect, the system and method implement a BMI that employs brain signals to interface with a computer or machine or automated system to determine the intent of a user and in particular the intent of a user located at an army vehicle crew station, for example. In one aspect, the disclosed system and method may reduce the numbers of people and their vehicles.

In one aspect, the disclosed system and method enables the operator of the army vehicles to handle increased information loads. Thus, aspects of the disclosed system and method provide a technique for rapidly determining an intended response of a user that can hand off some or all of the information burden to an automated system to handle it or hand it off to somebody else to handle while the user deals with the next event or the next piece of incoming information that the user must attend to. Accordingly, once the user decides that the event is either a threat, friendly, or neutral, the disclosed system and method can inform others of the identified event (e.g. a computer notifies the rest of the crew of the event). For example, if the event is a threat, the computer notifies the crew of the existence and location of the threat based on information gleaned from sensors and cameras pointed at the threat. Accordingly, based on the threat, the gunner bearing on the target associated with the identified threat can then look for other threats in the area. Further, while the gunner is engaging the threat, the user can be queueing up the next threat.

In various aspects, the disclosed system and method provides a non-invasive brain machine interface to identify and label an event as being a threat, friendly, or neutral. This technique can be extended to identifying and labeling three or more events that go beyond the conventional binary classification of an event being either a threat or nothing (e.g., no threat). The disclosed system and method provides three classes and two different modalities. So effectively, the system and method provides six different intent responses available to the user. It will be appreciated that the system and method can be expanded to more than three classes and more than two modalities as may be practical to implement.

Conventional implementations of non-invasive BMIs include the prosthetics domain where non-evasive sensors are employed to decode very low level instructions. An illustrative example of a prosthetic application includes someone with a prosthetic limb (robotic limb), such as an arm, with an EEG headset on their head that can use the prosthetic limb to try to reach out for an object (e.g. a cup). Conventional systems decode the person thinking about reaching for the cup and extract at relatively low information rates, the very low level instructions of moving the prosthetic arm. The series of machine instructions are analogous to instructions such as: extend the arm slightly, move it to the left, open the hand, move closer, close your hand, and other instructions. Execution of these types of low level discrete instructions is known as a direct control approach.

In contrast to the direct control approach, the disclosed system and method decodes the intent of picking up the cup rather than a series of discrete instructions to move the prosthetic arm. Rather than the machine decoding a plurality of discrete low level instructions from the user, which is extremely slow, the disclosed system and method provides a goal level approach where the machine is configured to directly decode the intended attempt to pick up the cup and hand that off to any computer and multiple different systems to execute instructions to accomplish the task. For example, once the user's intent to pick up the cup is identified, the machine can figure out how to reach out and pick up the cup. In one implementation, a camera can be used as machine vision to see the cup and determine the location of the robotic arm. The computer can use this information to move the robotic arm over the proper trajectory very quickly.

Furthermore, the disclosed system and method provides an auditory context in addition to EEG monitoring. In the auditory context, the user is instructed that there are three choices. One choice is to alert the gunner or slew the gunner as is commonly referred to in the art. Another choice is to launch an unmanned aerial vehicle (UAV). A third choice is to ignore it or in the disclosed paradigm, alert the bravo teams. The alpha team users located in their vehicle can be alerted to the correct response based on the range indicated in the auditory stimulus. In one example, an auditory alert such as "alpha team 500," can mean 500 meters (m), which can mean that the event is located outside the range of engagement. An auditory alert such as "alpha team 300" may be an instruction to the team that the event is located at 300 m and thus alert the gunner. Between 300 m and 1,000 m, for example, the instruction could be to launch an UAV with a camera for electronic surveillance of the event. An event beyond 1,000 m can be classified as being outside of the sphere of concern.

In various aspects, beyond immediate acquisition requirements, a ground vehicle may include a striker vehicle instrumented with multiple cameras and audio sensors so it can detect gun shots. The striker vehicle can include multiple cameras for the commander, the gunner, the driver, and can provide 360 degree vision.

FIG. 1 depicts a simulated crew station interface 100 for use with a BMI, according to one aspect of the present disclosure. The simulated crew station interface 100 comprises a split window interface including a wide pan view window 102, a narrow focus view window 104, and a user interface control panel window 106. In the wide pan view window 102, a wide view of a setting is depicted. The setting may include, for example, a desert comprising sand, a sky and a horizon. Graphical aspects of the setting may be generated by the simulated crew station interface 100. The simulated crew station interface 100 can provide a gimbal to a user of the BMI so that an object perceived through the gimbal may be rotated along an axis. The axis may be an axis selected from a group comprising a roll, pitch, and yaw axis. The user may use the gimbal to pivot the wide pan view window 102 along any of the roll, pitch, and yaw axis. The simulated crew station interface 100 may be configured to simulate the user performing reconnaissance for a simulated military crew. Accordingly, the user can monitor the wide pan view window 102 to perform reconnaissance. The crew can be simulated as being located in a crew vehicle 108 in the wide pan view window 102. The wide pan view window 102 depicts the crew vehicle 108 and a pointer 110 configured to be controlled by the gimbal.

In various aspects, the wide pan view window 102 can portray various visual stimuli. A visual stimulus may be, for example, a truck such as a flat bed truck, an armored fighting vehicle such as a tank, or a van such as a cargo van. As described later in further detail, identified visual stimuli may be categorized within a threat, a friendly, or a neutral category. In some aspects, the pointer 110 appears in the wide pan view window 102 as a rectangular shape enclosing a cross that intersects a circle may be used to focus on visual stimuli. The user may use the gimbal to control the pointer 110 by, for example, slewing or pivoting the gimbal in a particular direction to cause the pointer to move in a corresponding direction. Therefore, the user may use the gimbal to adjust the view depicted in the wide pan view window 102 to perform reconnaissance. When adjusting the view, the user may identify a visual stimulus. In various aspects, the BMI can be configured to automatically identify a visual stimulus and inform the user. In other aspects, the crew may initially identify a visual stimulus and inform the user. The visual stimulus may be identified based on adjusting the pointer 110 in a direction to detect the visual stimulus. Detecting by the pointer 110 may refer to, for example, slewing the pointer 110 such that the identified visual stimulus is located within the boundaries of the rectangular shape or the circle of the pointer 110. After the visual stimulus is identified, the eyes of the user may move from the wide pan view window 102 to the narrow focus view window 106. In some aspects, the narrow focus view window 106 may show a zoomed in view. A zoomed in view may refer to, for example, a narrow focus view comprising a magnified depiction of an area. The narrow focus view window 106 may depict a magnified depiction of the area enclosed within the pointer 110. The area enclosed within the pointer 110 can comprise a magnified visual stimulus, such as a truck 112 as depicted in FIG. 1. Although the magnified visual stimulus is shown as a truck 112, the magnified visual stimulus also may be an armored fighting vehicle, a van or any suitable visual stimulus located within the pointer in the pan view window 102.

Thus, the user initially may view a visual stimulus within the pointer 110. Subsequently, the user may slew the pointer 110 to identify the visual stimulus. The user may indicate interest in the identified visual stimulus based on the eyes of the user shifting to look at a larger depiction of the visual stimulus in the narrow focus view window 104. In some aspects, the eyes of the user may visually fixate on the identified visual stimulus for a predetermined time to indicate interest. The identified visual stimulus may be, for example, the truck 112. The BMI detects this eye movement via an eye tracking device and determines that the user is looking at an identified visual stimulus of interest. After the user focuses on the truck 112 in the narrow focus view window 104, the user thinks to formulate a response to the identified visual stimulus. The response may be, for example, to determine a category or class of the truck 112, such as whether the truck 112 is a threat, friendly, or neutral. In some aspects, the visual stimulus may instead be an auditory stimulus, as described later in further detail.

In various aspects, the BMI comprises an EEG device coupled to the brain of a user. The EEG device applies EEG to the user to detect electromagnetic signals generated by the brain of the user. The EEG device may comprise an EEG monitor coupled to a network of electrodes attached to the scalp encircling the brain of the user (see FIGS. 12-14 and 16, for example). As described below, the electrode network may be arranged in a standard layout such as a standard 10-10 electrode layout, along a cap that is disposed on the scalp of the user. The electromagnetic signals may refer to, for example, brain waves of the user. In particular, a plurality of neurons fires to transmit electromagnetic signals based on the occurrence of action potentials. The voltage difference between the plurality of firing neurons and a reference location can be measured by the network of electrodes and are amplified by an EEG amplifier. Therefore, EEG data can be sampled based on EEG channels corresponding to each electrode of the network of electrodes. In various aspects, when the brain of the user generates electromagnetic signals in response to the identified visual stimulus, the EEG may determine the intent of the user based on the generated electromagnetic signals. The intent of the user may be, for example, the formulated response. The intent of the user may be decoded by the BMI based on signal processing of the generated electromagnetic signals to determine whether the identified visual stimulus should be categorized as a threat, friendly or neutral. In various aspects, a delay in time occurs between the eyes of the user moving to look at the visual stimulus of interest and the user thinking to formulate a response to the identified visual stimulus. The delay may be any suitable delay such as, for example, 800 milliseconds (ms) or a range of delay times such as 600 ms to 1000 ms, for example.

The user interface control panel window 106 comprises graphical user interface (GUI) elements such as buttons. The user may activate a button to trigger a particular function of the BMI. In some aspects, the user interface control panel window 106 comprises various buttons, including the Mark Target 114, Mark Friendly 116, Mark Null 118, LRF 120, Cue Gunner 122, Slew Camera 124, Task UAV 126, Start 128, and Start Standalone 130 buttons. The user may activate the Start 128 button to cause a simulated trial of the BMI to begin. The user may activate the Start Standalone 128 button to cause a simulated trial in which the BMI does not decode the intent of the user. In various aspects, the user interface control panel window 106 may be configured to test the accuracy of the BMI decoding function. For example, the user may activate one or more of a group consisting of the Mark Target 114, Mark Friendly 116, and Mark Null 118 buttons to indicate that a visual stimulus has been incorrectly classified or categorized and should instead be categorized differently. Therefore, activating the Mark Target 114 button indicates the visual stimulus is in the threat class, the Mark Friendly 116 button indicates the visual stimulus is in the friendly class, the Mark Null 118 button indicates the visual stimulus is in the neutral class. Similarly, if the BMI inaccurately determines the intent of the user, the user may activate the LRF 120, Cue Gunner 122, Slew Camera 124, and Task UAV 126 buttons to indicate the corresponding correct user intent. The LRF 120 button indicates that a laser range finder (LRF) should be deployed. The Cue Gunner 122 button indicates that a gunner should be alerted, for example, so that the gunner can be ready to fire a gun at a threat. The Slew Camera 124 button indicates that a camera should be slewed, for example, to focus on a visual stimulus. The Task UAV 126 button indicates that an unmanned aerial vehicle (UAV) should be launched, for example, to aerially monitor a visual stimulus.

Figure 2:
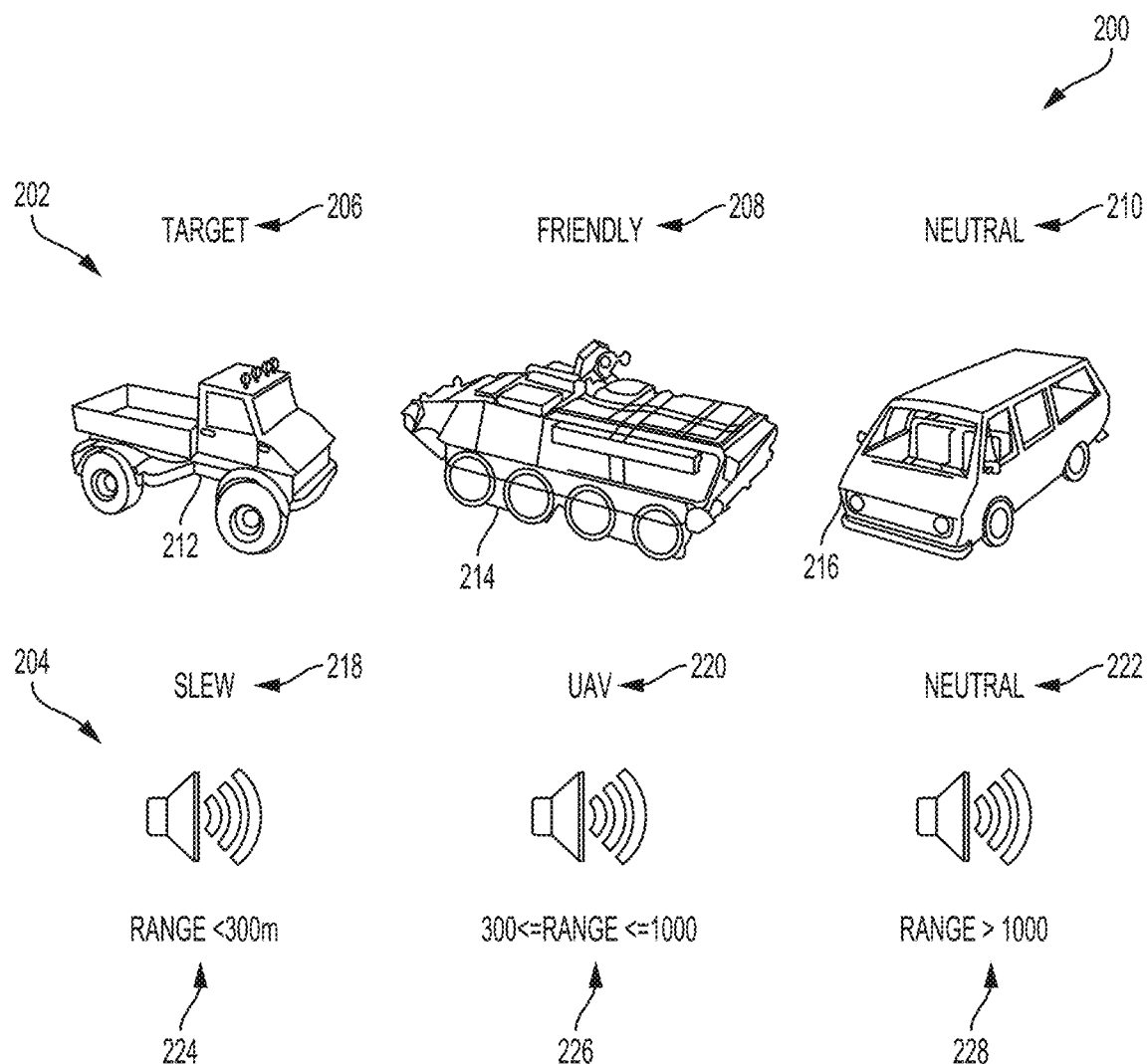
FIG. 2 is a diagram of a classification of user intended responses to visual and auditory stimuli, according to one aspect of the present disclosure.

FIG. 2 is a diagram of a classification 200 of user intended responses to visual and auditory stimuli, according to one aspect of the present disclosure. In various aspects, the top row 202 depicts a set of various visual stimuli such as a truck 212, an armored fighting vehicle 214, and a van 216 and a first plurality of possible classes of responses such as target 206, friendly 208, and neutral 210 for a first attentional context. The first attentional context may be, for example, a visual context. In some aspects, the bottom row 204 depicts various ranges of auditory stimuli in a low range 224 less than 300 m, in a mid range 226 between 300 m and 1000 m, and in a high range 228 greater than 1000 m and a second plurality of possible classes of responses such as slew a gunner 218, launch a UAV 220, and treat auditory neutral 222 for a second attentional context. The second attentional context may be, for example, an auditory context. As disclosed with reference to FIG. 1, the various stimuli may be a truck 212, armored fighting vehicle 214, van 216, or any suitable visual stimulus. The first plurality of possible classes of responses can include a threat 206, a friendly 208, or a visual neutral 210 class. The various ranges of stimuli may be a low 224, mid 226, or high 228 range. The treat auditory neutral 222 class may refer to, for example, alerting a military response team such as a bravo team that further investigation of a stimulus may be required. In some aspects, the various ranges of stimuli may constitute auditory cues such as sounds or other factors that indicate the relative location of a stimulus. For example, an auditory event such as the sound of footsteps can be tracked from a crew station by auditory volume detector device to indicate that a stimulus is located within 300 m of a crew station.

In some aspects, two or more of the set of various stimuli 212, 214, 216 and the various ranges of stimuli 224, 226, 228 may be variants of a same type of stimulus. For example, the truck 212 and the low range 224 both may be threat type stimuli, the armored fighting vehicle 214 and the mid range 226 both may be friendly type stimuli, and the van 216 and the high range 228 both may be neutral type stimuli. The use of visual context variants and auditory context variants of the same type of stimulus can ensure that the BMI does not detect a single type of response to a particular type of stimulus rather than actually detecting or decoding the intent of the user. With reference to FIG. 1, in some aspects, the eye tracking device may be used for the visual context, while the auditory volume detector device may be used for the auditory context. In various aspects, while the user is looking at the wide pan view window 102 of the simulated crew station interface 100 as disclosed with respect to FIG. 1, the BMI may communicate auditory stimuli to the user. The auditory stimuli may be communicated in a manner similar to audio communicated over a radio channel. Based on the auditory volume detector device (e.g., a microphone), the BMI may detect when auditory stimuli are communicated. This detection by the BMI may be used to determine whether the user is listening to an auditory stimulus of interest.

In various aspects, additionally or alternatively, the user may perform some action that indicates the user has heard an auditory stimulus of interest. In various aspects, the user thinks to formulate a response to the auditory stimulus of interest. The response may be, for example, to determine a class of the auditory stimulus of interest. As previously disclosed in FIG. 2, the class may be selected from the second plurality of possible classes of responses 218, 220, 222. Similar to the disclosure with reference to FIG. 1, the EEG device of the BMI may apply an EEG to determine the intent of the user based on signal processing of the generated electromagnetic signals. The intent of the user may be, for example, the formulated response. In various aspects, a delay in time occurs between the user detecting the occurrence of the auditory stimulus of interest and the user thinking to formulate a response to the auditory stimulus. The delay may be any suitable delay such as, for example, 800 ms, or a delay in the range of 600 ms to 1000 ms. In various aspects, as described below in further detail, the BMI may be context multimodal such that the user can perceive stimulus in either or both the visual and auditory contexts (i.e. auditory or visual stimuli). In addition, the user can shift attention between the contexts. In other words, the user can switch from paying attention or allocating a majority of attention to a visual stimulus to an auditory stimulus. Alternatively, the user can switch from paying attention or allocating a majority of attention to an auditory stimulus to a visual stimulus. The BMI can determine such a shift in attentional context by the user through linear discriminate analysis, as further described later in connection with FIGS. 3 and 4.

Figure 3:
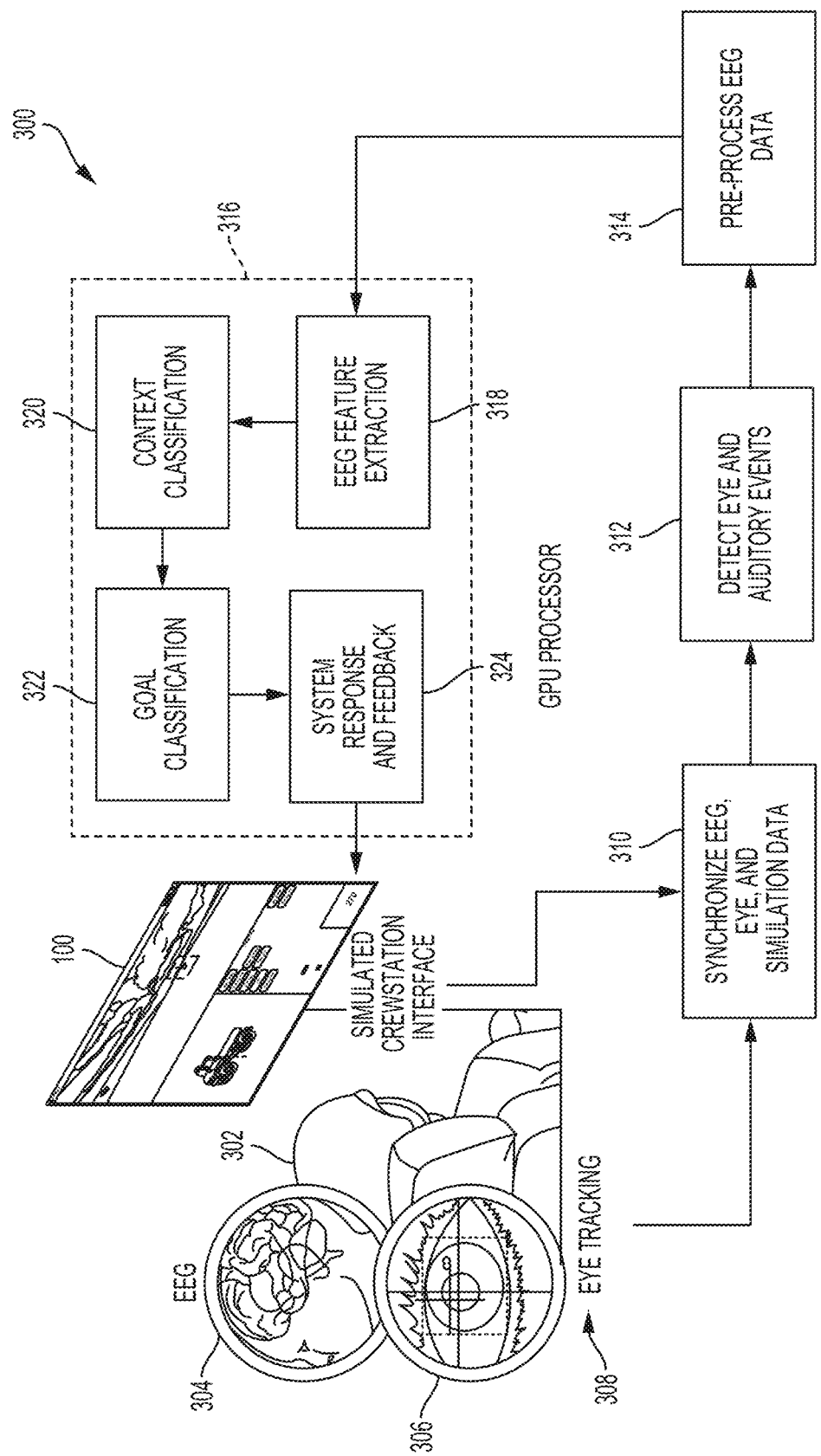
FIG. 3 is a diagram of a BMI system using an EEG device and an eye tracking device to detect the cognitive or behavioral goals of the user of a BMI in order to improve the quality of BMIs, according to one aspect of the present disclosure.
Figure 16:
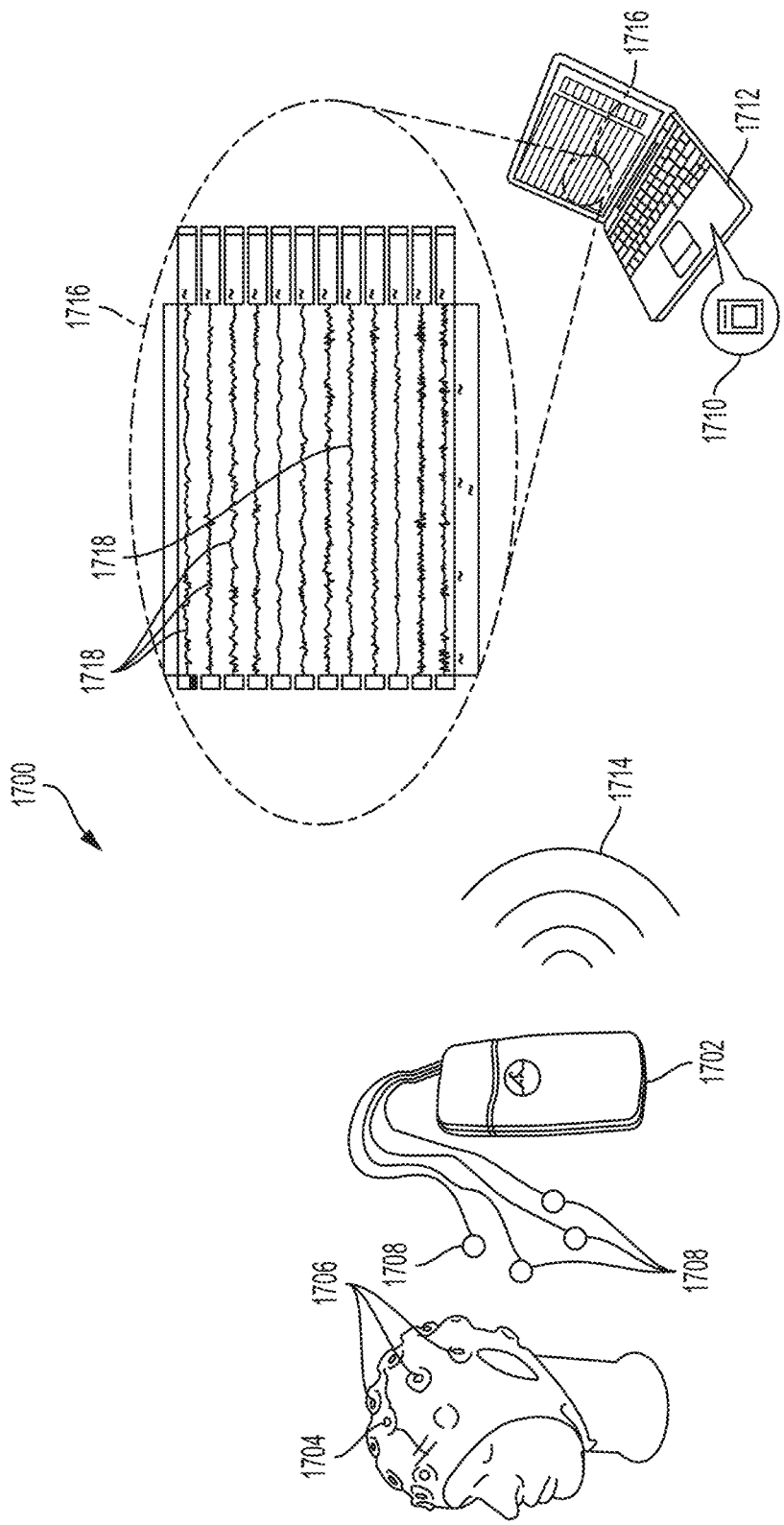
FIG. 16 shows one aspect of a MOBITA-W-32EEG EEG system comprising a wearable physiological signal amplifier system that records 32 channels of high-fidelity wireless EEG data with water based electrodes, according to one aspect of the present disclosure.

FIG. 3 is a diagram of a BMI system 300 using an EEG device 302 and an eye tracking device 308 to detect the cognitive or behavioral goals of the user of a BMI in order to improve the quality of BMIs, according to one aspect of the present disclosure. Detecting the cognitive or behavioral goals of the user may include detecting the intent of the user. The EEG device 302 comprises EEG electrodes noninvasively attached to the scalp of the user. The EEG device 302 is configured to apply 304 an EEG test to the user. The EEG device 302 may be a wireless 32-channel EEG system such as, for example, MOBITA-W-32EEG available from Biopac Systems, Inc. of Goleta, Calif. Turning briefly to FIG. 16, there is shown one aspect of a MOBITA-W-32EEG EEG system 1700 comprising a wearable physiological signal amplifier system that records 32 channels of high-fidelity wireless EEG data with water based electrodes 1708, according to one aspect of the present disclosure. The EEG system 1700 includes a MOBITA base unit 1702 with onboard 3D accelerometer and trigger channel, a configuration cap configured for 32-Channel EEG, a head-cap 1704 with 32 grommets 1706 to receive the water based electrodes 1708, water based electrodes 1708, and software 1710 that runs off a general purpose computer 1712. The MOBITA EEG system 1700 is configured to record wireless EEG signals for brain-computer interfacing or BMI. The MOBITA EEG system 1700 can record many different signal types. In some aspects, the electrode configuration or signal type may be quickly changed by swapping out the configuration cap. The MOBITA EEG system 1700 can telemeter 1714 data back to the general purpose computer 1712 running software 1710 for real-time display 1716 and analysis of the signals 1718, or record it locally in a memory of the base unit 1702 for later download to the computer 1710. The MOBITA EEG system 1700 can switch between WiFi mode, logger mode, or hybrid mode to suit a particular application protocol. The MOBITA EEG system 1700 is battery operated, rechargeable, and its compact size, integrated WiFi connectivity and flexibility are combined in a mobile physiologic measurement device.

With reference now back to FIG. 3, in various aspects, the active electrodes of the EEG device 302 may be arranged in a standard 10-10 electrode layout or any other suitable arrangement of electrodes on the scalp of the BMI user. The standard electrode layout can be used for mapping out various areas of the brain such as the temporal lobe, occipital lobe and parietal lobe. In other words, each electrode in the layout corresponds to an area or subarea of the brain. As previously described, the electrodes of the layout may measure voltage difference between the plurality of firing neurons and a reference location based on the electromagnetic signals generated by firing neurons of the brain of the BMI user. The EEG data generated by the EEG device 302 may be transmitted over the Transmission Control Protocol/Internet Protocol (TCP/IP) communication protocol or any other suitable protocol. The eye tracking monitor 306, such as, for example, a camera, smartphone, or computer, is configured to track 308 the eye movements of the user to generate eye tracking data. In some aspects, the eye tracking monitor 306 is a near-infrared illumination and camera device attached to a crew station desktop computer. Eye tracking data may be transmitted over the User Datagram Protocol (UDP) communication protocol. The eye tracking monitor 306 can sample eye tracking data at a 250 Hz sampling rate. Other eye tracking sampling rates may be selected between 50 Hz to 500 Hz, for example. Auditory events may be monitored by the auditory volume detector device, such as, for example, a sound detection circuit comprising a microphone, amplifier, and microcontroller. In addition, the BMI system 300 may comprise biometric sensors to detect biometric data associated with the BMI user. For example, the biometric sensors may detect movements in the body parts of the BMI user and/or physiological changes of the BMI user such as increased rates of sweating. This biometric data may be processed and communicated to the BMI.

With reference now to FIGS. 1 and 3, a subject user monitors an interface such as, for example, the simulated crew station interface 100, for visual and auditory stimuli of interest. The attention of the user may shift between visual and auditory stimuli. Such shifts may be detected in order to classify 320 the attentional context, as described further below. In various aspects, a computer of the BMI system may implement the simulated crew station interface 100. The computer may be configured to execute a custom unity application to provide the stimuli and feedback. The computer can synchronize 310 EEG, eye, and simulation data using any suitable software program to ensure all the data is measured or generated on a consistent time scale. In various aspects, the EEG data, eye tracking data, and data associated with the simulated crew station interface 100 may be transmitted over a common network. Synchronizing may refer to common event signaling over the common network. Common event signaling can be attained by determining the common time at which each instance of EEG, eye tracking, and simulation interface data indicate that the user of the BMI is aware of a visual stimulus of interest or has formulated a response to the visual stimulus of interest. In various aspects, auditory data also may be synchronized. As disclosed with reference to FIGS. 1-3, the eye tracking device 308 is configured to detect 312 eye fixation events and the auditory volume detector device is configured to detect auditory events. In aspects, an eye fixation event refers to the BMI user becoming aware of a visual stimulus of interest by looking and fixating on the visual stimulus and an auditory event refers to the BMI user becoming aware of an auditory stimulus of interest by listening to the auditory stimulus. The eye tracking device 308 may detect an eye fixation event based on one or more position and velocity measurements. An eye fixation event detection algorithm may comprise the one or more position and velocity measurements. The auditory volume detector device may detect an auditory event by sensing auditory output from the crew station.

In various aspects, a suitable bandpass filter of the BMI system 300 is used to pre-process 314 by filtering the EEG data such as, for example, to allow only frequency channels of the EEG data within the frequency range of 1 Hz to 50 Hz. Therefore, the filtering can be low pass filtering. The frequency channels for each EEG channel may be segmented into frequency bands such as the following example bands: a delta frequency band ranging from 1 Hz to 4 Hz; a theta frequency band ranging from 4 Hz to 8 Hz; an alpha frequency band ranging from 8 Hz to 14 Hz; a beta frequency band ranging from 13 Hz to 30 Hz; and a gamma frequency band ranging from 30 to 40 Hz. It is well known that these EEG frequency bands indicate different information about the functioning of a brain, such as emotional and neurological characteristics of contemporaneous brain function. The EEG data may be generated by the network of electrodes disposed on the scalp of the user. The network of electrodes can conduct electromagnetic signals generated from the brain of the user to an amplifier to display on the EEG monitor of the EEG device (e.g., the MOBITA EEG system 1700 shown in FIG. 17). As previously described, the electrode network corresponds to EEG channels. The electric potentials corresponding to the EEG channels can be monitored. In addition, the filtered EEG data may be re-referenced to linked mastoid channels acting as reference locations for the voltage difference measured for each EEG channel. A first linked reference electrode may be placed on a right mastoid bone of the user and a second linked reference electrode may be placed on a left mastoid bone of the user. Therefore, a difference in each of the monitored electric potentials may be defined or determined relative to the base level of the linked reference electrodes. A differential amplifier may be used with the electrodes and the linked reference electrodes to filter out noise such as electrical activity not specific to the brain, for example, a change in electric potential caused by sweating of the user. A determined difference in electric potential between an EEG channel and the linked mastoid channels may correspond to activity in the area of the brain corresponding to the location of the electrode on the scalp corresponding to the EEG channel. The frequency of the brain waves of the EEG data corresponding to the electrode can indicate the extent of activation of the corresponding area of the brain.

In one aspect, the pre-processing 314 can be nearly instantaneous. The pre-processing 314 can maximize the signal-to-noise ratio (SNR) of the EEG data. In various aspects, for each EEG channel, the EEG data may be segmented into blocks of data to, for example, focus on the portions of EEG data corresponding to the stimulus of interest. Because the EEG data is time nonstationary, such that the spectrum of the EEG data changes over time, the EEG data may be segmented based on intervals of time. The time intervals may be, for example, EEG data sampled over a one second time interval (e.g., 1 Hz) or bins. Segmenting the EEG data based on suitable time intervals or bins generates a sequence of EEG data segments. In some aspects, when a BMI user indicates interest in a visual stimulus, the eye fixation event can be a point for defining a time interval used to segment the EEG data into blocks. The eye fixation event can be determined based on using eye fixations of the user to measure brain responses of the user to visual stimuli. Similarly, the BMI can identify when an auditory stimulus is communicated to the user to define a time interval.

In various aspects, a graphics processing unit (GPU) processor 316 of the BMI system 300 is configured to extract 318 EEG features from the pre-processed EEG data, classify 320 the attentional context, classify 322 the goal and the intended user response, and generate 324 system response and feedback. It will be appreciated that the GPU processor 316, occasionally called a visual processing unit (VPU), is a specialized electronic circuit designed to rapidly manipulate and alter memory to accelerate the creation of images in a frame buffer intended for output to a display device. The GPU processor 316 may be located in embedded systems, mobile phones, personal computers, workstations, and game consoles. The GPU processor 316 efficiently manipulates computer graphics and image processing based on the EEG data, and includes a highly parallel structure that makes it more efficient than general-purpose central processing units (CPUs) for algorithms where the processing of large blocks of data is done in parallel. In a personal computer, a GPU processor can be present on a video card, or it can be embedded on the motherboard or, in certain CPUs, on the CPU die. The GPU processor 316 is available from a variety of sources such as, for example, Intel, Nvidia, AMD/ATI S3 Graphics (owned by VIA Technologies), and Matrox. Additionally or alternatively, a field-programmable gate array (FPGA), computer, or other suitable integrated circuit (IC) may perform the functions of the GPU processor 316.

In various aspects, the GPU processor 316 can extract 318, for example, higher order spectral features based on feature sources such as phase or amplitude of the EEG data. Higher order spectral features may be, for example, bispectrum features. Extraction can be achieved by applying a continuous wavelet transform (CWT) such as a Morlet wavelet transform to the segmented EEG data. In other aspects, other suitable signal processing methods such as short-time Fourier transform (STFT) or discrete wavelet transform (DWT) can be used in conjunction with the Morlet wavelet. The Morlet wavelet transform is defined as the inner product or convolution of the Morlet wavelet function and the segmented EEG data. Conventional Fourier analysis only decomposes EEG data to determine the frequency components of the EEG data. Determination of the temporal components of the EEG data does not occur in traditional Fourier analysis. Moreover, conventional Fourier analysis does not analyze the non-stationary aspect of the EEG data provide information. In other words, the time varying frequency characteristics of the EEG data within a particular EEG channel and across EEG channels are not detected due to the poor temporal resolution of Fourier analysis. In contrast, the Morlet wavelet transform decomposes the EEG data with respect to frequency and time simultaneously based on the scale and tau parameters of the Morlet wavelet transform. Therefore, the Morlet wavelet transform generates information representing the time varying frequency characteristics of the EEG data for a particular channel and the interactions between time varying spectra of two or more EEG channels. Moreover, unlike conventional Fourier analysis, the Morlet wavelet transform may be used to detect interactions between EEG channels with respect to phase, amplitude, frequency, and/or time.

As described in further detail with reference to FIG. 4, the bispectrum features refer to a wavelet bispectrum calculation for every possible pair of EEG channels. The wavelet bispectrum calculation represents the degree that the two EEG channels of a particular pair of EEG channels, or frequency components within a particular EEG channel are phase correlated or synchronized to each other. For example, for a particular pair of EEG channels, the plurality of bispectrum features corresponding to the particular pair would quantify the degree of phase coupling information for the particular pair of EEG channels. As previously described, in various aspects, the wavelet bispectrum calculation can be calculated for every possible different pair of EEG channels. Thus, the bispectrum feature space consists of the total plurality of bispectrum features corresponding to every possible paired combination of EEG channels and every EEG channel individually. The bispectrum feature space can be used to observe short-time dynamics and the salient nonlinear interactions between various pairs of EEG channels. The wavelet bispectrum calculation also may be calculated within one EEG channel for each of the EEG channels. In other words, the wavelet bispectrum calculation can represent the extent to which two time varying frequencies are phase correlated with respect to their sum (or difference). As described further in FIG. 4, the wavelet bispectrum can analyze EEG data of two EEG channels to represent the degree that the phase angles of two frequencies $f_1$ and $f_2$ present in one EEG channel are correlated to the phase angle of the frequency that is equal to the sum (or difference) of $f_1$ and $f_2$ in the other EEG channel. In addition, the wavelet bispectrum can analyze the spectral amplitude for each frequency $f_1$ and $f_2$ as well as the sum (or difference) of $f_1$ and $f_2$. The calculated wavelet bispectrum is a complex number such that the magnitude of the calculated wavelet bispectrum indicates the strength of the phase angle correlation between the frequencies $f_1$ and $f_2$ and their sum or difference and the spectral amplitudes corresponding to those frequencies.

This wavelet bispectrum calculation is repeated for all frequencies represented in the respective Morlet wavelet transforms of the two EEG channels. Therefore, variation in phase angle correlations between the frequencies of the two EEG channels can be measured by the amplitude and phase of the wavelet bispectrum. Specifically, the phase of the bispectrum can be applied across multiple channels and frequency interactions to determine the intent of a BMI user with a high degree of accuracy, such as by creating a bispectrum feature space that can be used to discriminate between multiple intended responses of the user. As previously described, the temporal variation of nonlinear interactions between the two EEG channels can be observed since the wavelet transform retains temporal information. Using the GPU processor 316 to extract 318 bispectrum features of the segmented EEG data for every possible pair of EEG channels can be used to analyze the time-varying and nonlinear harmonic interaction of the EEG signals.

In various aspects, to classify 320 the attentional context, the GPU processor 316 analyzes data from multiple user subjects of the BMI in a first training set process to select features from the feature space. Features can be selected so as to provide the best segregation between different intended responses of the multiple subjects (corresponding to an attentional context) and the phase of bispectrum. The training set process can comprise partitioning the feature space into subsets and training the BMI to recognize the effect of a user subject identified stimulus of interest for each subset of the feature space. Cohen's d may be used to compare and evaluate effect sizes of each subset. It will be appreciated that Cohen's d is an effect size used to indicate the standardized difference between two means. Cohen's d is an appropriate effect size for the comparison between two means. As described below in further detail, the training sets can comprise both an auditory trial training component and a visual trial training component. Any suitable number of trials may be used to classify 320 the context. When used in conjunction with Cohen's d, the set of auditory trials can be used to identify how feature space subsets correspond to user recognition of and response to auditory stimuli and the set of visual trials can be used to identify how feature space subsets correspond to user recognition of and response to visual stimuli. As previously described, in various aspects, the BMI can be multimodal such that the occurrence of both auditory and visual stimuli can overlap and/or the user can shift attention between auditory and visual stimuli. In some aspects, some feature space subsets correspond to shifts in user attention between auditory and visual stimuli. The training sets and Cohen's d can be used to select the subset of features that best correspond to user recognition of auditory and visual stimuli, respectively. The selected subset can be used to construct a feature vector. As described later, the GPU processor 316 may use a discriminate classifier to apply linear discriminate analysis to classify 320 the shifts in attentional context.

Similarly, to classify 322 the intended user response, the GPU processor 316 analyzes data from multiple user subjects of the BMI in a second training set process to select features from the feature space. In some aspects, the second training set process may sequentially follow the first training set process. However, in other aspects, the first and second training set processes may occur simultaneously such that all the selected features are selected in one process. The training set process can comprise partitioning the feature space into subsets and training the BMI to recognize the effect of a response to a user subject identified stimulus of interest for each subset of the feature space. As previously described, the BMI may classify 322 the user response as a threat 206, a friendly 208, or a visual neutral 210 for identified visual stimuli and to classify 322 the user response as slew a gunner 218, launch a UAV 220, or treat auditory neutral 222 for identified auditory stimuli based on whether the identified auditory stimuli is low 224, mid 226, or high 228 range. The training sets and Cohen's d can be used to select the subset of features that best correspond to the user response to identified auditory and visual stimuli, respectively. Any suitable number of trials may be used to classify 322 the goal. The selected subset can be used to construct a feature vector for classification. As described later, the GPU processor 316 may use a discriminate classifier to apply linear discriminate analysis to classify 322 the user responses to particular visual or auditory stimuli based on a discriminate classifier applying linear discriminate analysis. The BMI may generate 324 system response and feedback based on the success of the linear discriminate analysis classification. In some aspects, unsuccessful classification may be used to implement further training set processes. In addition, unsuccessful classification may be used to adjust parameters or sensitivity of the simulated crew station interface 100.

Figure 4:
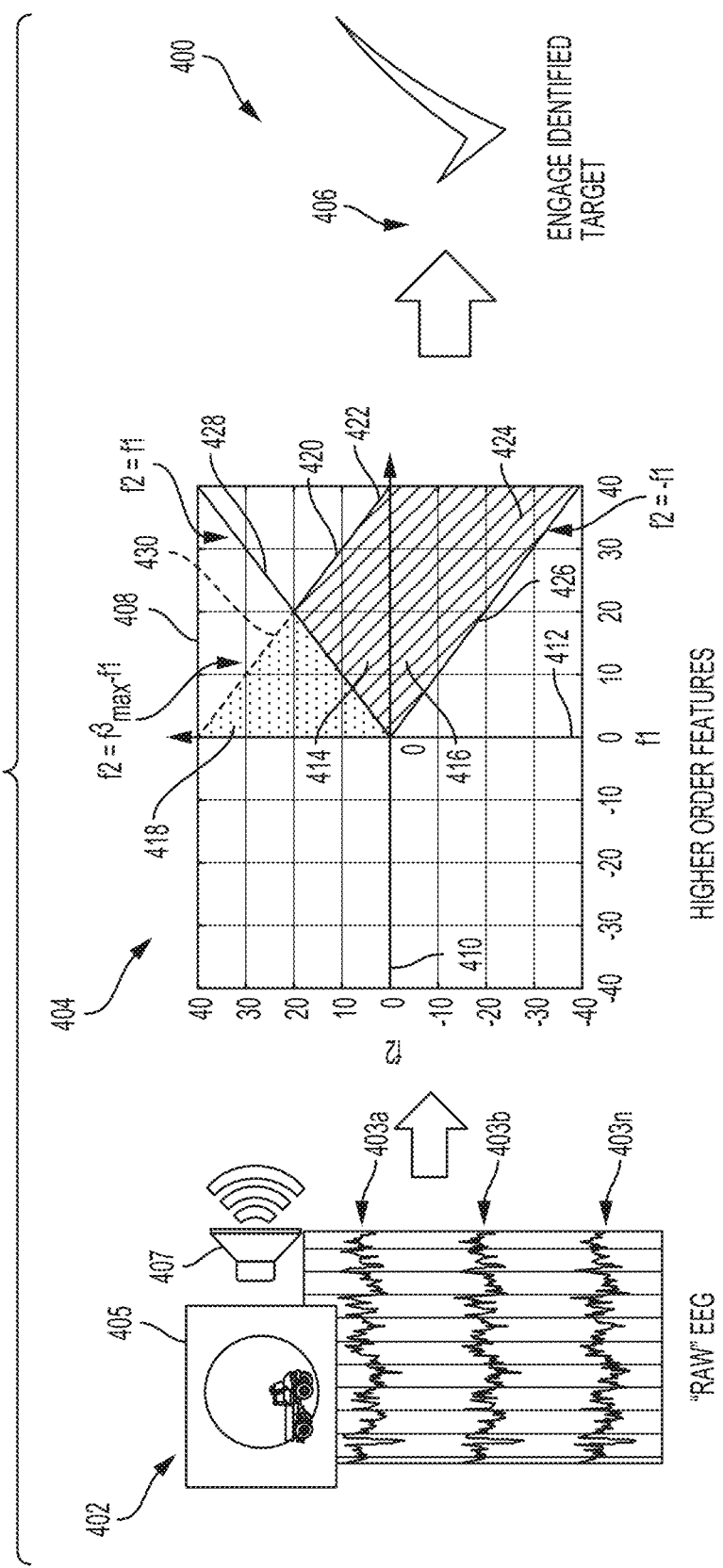
FIG. 4 shows the extraction and selection of bispectrum features as well as context and goal classification in more detail, according to one aspect of the present disclosure.

FIG. 4 shows the extraction and selection of bispectrum features as well as context and goal classification in more detail, according to one aspect of the present disclosure. In various aspects, the extraction and selection may be performed to measure non-linear phase coupling to classify 320 the context and classify 322 the goal given the short-term non-stationarity of the EEG data. FIG. 4 depicts a process 400 to detect 402 raw EEG signals 403a, 403b, 403n from visual 405 and auditory 407 stimuli (where n is a positive integer), extract 404 higher order features from the raw EEG signal 403a-n, and engage 406 the identified target. A Morlet wavelet transformation is applied 404 to the raw EEG signals 403a-n to calculate the bispectrum, extract 404 the bispectrum features, select a subset of wavelet bispectrum feature space, classify 320 the attentional context, and classify 322 the user intended response, as shown in FIG. 3. According to various aspects, as previously described, the EEG device 302 of the BMI can detect 402 raw EEG signals 403a-n during the time in which the BMI user identifies various stimuli of interest, such as visual stimuli 405 and auditory stimuli 407, and formulates different responses or behavioral goals to the identified stimuli 405, 407, such as: engaging a target, communicating with a friendly vehicle, or ignoring neutral elements in the scene. After segmenting the EEG data based on predetermined time intervals, the BMI can apply a CWT such as the Morlet wavelet transformation to each EEG channel of the segmented EEG data to obtain a time-scale representation of the non-stationary segmented EEG data. For the time-scale representation, time can be measured according to a tau parameter and scale is inversely related to frequency.

The extraction 404 of the higher order features can be explained by analyzing the graph 408 where the x-axis 410 represents a first frequency $f_1$ and the y-axis 412 represents a second frequency $f_2$ of the raw EEG signals 403a-n detected 402 from the visual 405 and auditory 407 stimuli. The graph 408 defines four regions, a summation region 414 ($f_1+f_2$), a difference region 416 ($f_1-f_2$), a symmetric region 418, and a principal region 420. The summation region 414 is defined as the shaded area between the positive x-axis 410 and the line $f_2=f_1$. The difference region 416 is defined as the shaded area between the positive x-axis and the line $f_2=-f_1$. The symmetric region 418 is defined as the shaded area between the positive y-axis, the line $f_2=f_{3max}-f_1$, and the line $f_2=f_1$. The high frequency bispectrum 422 can be extracted from the summation region 414 and the low frequency bispectrum can be extracted from the difference region 416.

The wavelet bispectrum may be calculated and used to extract 404 bispectrum features for intra-channel (i.e., calculated for one EEG channel in isolation) and inter-channel (i.e., calculated for a particular pair of EEG channels). In various aspects, the bispectrum feature space consists of the total plurality of bispectrum features corresponding to every possible combination of pairs of EEG channels and every EEG channel individually. The bispectrum feature space can be used to observe short-time dynamics and the salient nonlinear interactions between various pairs of EEG channels. The wavelet bispectrum calculation also may be calculated within one EEG channel for each of the EEG channel. For two EEG channels X and Y, the wavelet bispectrum between channel X ($C_X$) and channel Y ($C_Y$) is defined as:

$$B_{X,Y}^W(f_1,f_2) = \int_T (f_1,\tau) W_X(f_2,\tau) W^*_Y(f_3,\tau) d\tau \quad (1)$$

where frequencies $f_1$, $f_2$, and $f_3$ satisfy the frequency sum rule: $f_3=f_1+f_2$, $W_x(f, \tau)$ and $W^*_y(f, \tau)$ denote the complex Morlet Wavelet transform of $C_X$ and $C_Y$ at frequency f. $W^*_Y(f_3, \tau)$ is the complex conjugate of the $f_1$ and $f_2$. The wavelet bispectrum is a wavelet that represents the extent of phase coupling or synchrony over time between $f_1$, $f_2$ and their sum $f_3$. Therefore, the strength of the interaction between the respective frequencies of $C_x$ and $C_y$ is measured by the normalized amplitude (bi-coherence) and phase (bi-phase) of the bispectrum (Eq. 1).

The bi-coherence can be used to measure the change in power (amplitude) of the bispectrum over various time bins. The bi-phase may indicate the existence of nonlinear (e.g. quadratic) phase coupling. In particular, for frequencies $f_1$, $f_2$, and $f_3$ satisfying the frequency sum rule specified above, the phase of a sum (or difference) sinusoid component at frequency $f_3$ equals the phase of a first sinusoid component at frequency $f_1$ and the phase of a second sinusoid component at frequency $f_2$. In some aspects, the bi-phase indicates the extent to which the phase angles of $f_1$, $f_2$, and $f_3$ are aligned or phase coupled. As previously described, the EEG phase coupling may refer to intra-channel or inter-channel phase coupling such that, for example, the sinusoid component at $f_3$ exists in the same or a different EEG channel as the sinusoid components at frequencies $f_1$, $f_2$. In aspects, this phase coupling may indicate that the sinusoid components at frequencies $f_1$, $f_2$ are commonly generated by or commonly synthesize the sinusoid component at frequency $f_3$. The sinusoid components at frequencies $f_1$, $f_2$ may correspond to an increase or decrease in bi-coherence from one time bin to another time bin. Based on these calculations, the GPU processor 316 may extract 406 bispectrum phase features for all EEG channels individually and for every possible pair of EEG channels. Thus, the bispectrum feature space consists of the total plurality of bispectrum phase features corresponding to every possible combination of pairs of EEG channels and every EEG channel individually.

In various aspects, EEG data collected from the wireless 32-channel active electrode EEG system 302, eye fixation data from the eye tracking device 304 operating at 250 Hz from 15 BMI user subjects performing the stimuli identification tasks at the simulated crew station interface 100, and auditory data from the auditory volume detector device are used to select 408 a subset of wavelet bispectrum features from the bispectrum feature space. More specifically, as previously described, a training set process comprising an auditory trial training component and a visual trial training component can be applied. The selected subset of features from the bispectrum feature space can be the features that most correspond to the user identification of visual stimuli or auditory stimuli and the user intended response to the identified stimuli. For training in the visual attentional context, user subjects are to identify the stimulus as a type of visual stimuli and generate an intended response to the identified visual stimulus. As previously described, visual stimuli can include a truck 212, armored fighting vehicle 214, and van 216. BMI users may intend to respond to identified visual stimuli as a threat 206, a friendly 208, or a visual neutral 210. For training in the auditory modality context, user subjects are to listen to an auditory stimulus and respond based on whether the range of the auditory stimulus belonged to the low 224, mid 226, or high 228 range categories. As previously described, responses to auditory stimuli can include slewing a gunner 218, launching a UAV 220, or treating the auditory stimulus neutral 222.

The training results may be applied to select 408 subset from the bispectrum phase feature space. Specifically, each pair of EEG channels and frequencies over all time bins represented in the bispectrum phase feature space is analyzed with Cohen's d to determine the bispectrum features that are consistent with the user subject identifying an auditory or visual stimulus or formulating a response to the identified stimulus. Based on eye fixations and sound detection, respectively, the eye tracking device 304 and auditory volume detector can indicate the time bins or epochs corresponding to when an auditory or visual stimulus has been identified device. Cohen's d may be applied to determine the effect size for various bispectrum features before and after the identified stimulus. More specifically, feature generation includes segmenting EEG signals into overlapping epochs ($T_E$); computing wavelet transform across desired frequency range (3-40 Hz); computing (1) for each channel-pair and bi-frequency combination over each epoch; determining the optimal feature set based on the Cohen's D Effect Size; generating feature signature $G=\{T_E, f_1, f_2, f_3, C_X, C_Y, b_{X,Y}(f_1, f_2) f(f_1, f_2)\}$. Additional training sets may be completed as necessary.

In some aspects, based on the training, the bispectrum phase features are ranked by their consistency with user identification of attentional context and the GPU processor 316 selects 408 a predetermined number of the most consistent bispectrum features. The selected subset can be used to construct a feature vector. The feature vector may be input into a linear discriminate classifier to classify 320 the attentional context. The linear discriminate classifier may generate a hyperplane that partitions the feature vector into a partition that corresponds to visual stimuli and a partition that corresponds to auditory stimuli. As previously described, the BMI may be multimodal such that a BMI user may encounter either or both auditory and visual stimuli. For example, in aspects, the user may visually perceive a truck 212 and also hear engine noise. In such aspects, the GPU processor 316 may use the hyperplane, machine learning, and a weighed classification system to determine the degree of attention the user allocates to auditory and visual stimuli, respectively. For example, as described with reference to FIGS. 8 and 9, the hyperplane may be used to identify pairs of frequencies (in the bispectrum feature space) that correspond to identified auditory or visual stimuli, respectively. In some aspects, the weighted classification system and machine learning can be used for enabling the BMI to quantify the relative contribution of those identified frequency pairs that correspond to identified auditory or visual stimuli. In other words, a weight may be assigned to each of the various identified frequency pairs of the selected features based on the extent that each pair correlates to user attention allocated to stimuli in the auditory and visual attentional contexts. In aspects, as described further in FIG. 5, by applying the classifier to additional test data for classifier regularization, the classifier may reduce the number of bispectrum phase features inputs necessary to classify 320 the attention context, based on the weights assigned to relatively higher correlated frequency pairs of the selected bi-spectral features.

Similarly, based on the training, the GPU processor 316 can select another subset of bispectrum phase features based on the correlation between variation in the phase of each of the bispectrum phase features and user intended response, for the time bins corresponding to user response to identified stimuli. Accordingly, the bispectrum phase feature space may be ranked to select the subset of bispectrum phase features with the best correlation to user response. After the GPU processor 316 selects a predetermined number of the most correlated bispectrum phase features, the selected subset can be used to construct a feature vector. The feature vector may be input into the linear discriminate classifier to classify 322 the user intended responses. The linear discriminate classifier may generate a hyperplane that partitions the feature vector into a partition that corresponds to visual stimuli and a partition that corresponds to auditory stimuli. The linear discriminate classifier may be applied for three classes (i.e., three user responses for either of the two attentional contexts). In other aspects, the linear discriminate classifier may be applied for six classes (i.e., six possible responses for both attentional contexts). For each selected bispectrum feature, the discriminate function of the linear discriminate classifier calculates the conditional probability that the selected bispectrum phase feature should be classified within each of the possible user response classes. Therefore, the GPU processor 316 can determine the user response class for each selected bispectrum feature. In various aspects, as described further in FIG. 6, the GPU processor 316 may apply classifier regularization by applying the classifier to additional test data for classifier regularization such that the classifier may reduce the number of bi-spectral features inputs necessary to classify 322 the user intended responses. In other words, multiple bispectrum phase features may be correlated with a user intended response, but not all correlated bispectrum features are necessary to successfully classify 322 the user intended responses. Therefore, classifier regularization may be for reducing the number of correlated bispectrum phase features to the minimum number necessary to successfully classify 322 the user intended responses.

Classification performance for determining the attentional context averaged 91.8% (chance=50%) across subjects. Classification performance in selecting the target goal to auditory stimuli averaged 94.3% (chance=33%), and 98.0% (chance=33%) in the visual modality.

Still referring to the EEG-based classification of intended responses in a multi-modal crew station simulation, brain-computer interfaces (BCIs) show great promise in augmenting people's abilities. Noninvasive approaches such as EEG have two fundamental control signals. The first is direct control which uses scalp potentials to decode the details of motor execution (position, velocity, angle, etc.) measured in primary motor cortical areas. The alternative control approach is goal selection. In a goal-directed BMI, goals are selected by detecting neural signals associated with the user's behavioral goals, while the machine enacts the details normally controlled by finer-grain motor commands. To develop the goal-directed BMI in accordance with the present disclosure, the ability to decode the intent of a subject's performing identification tasks in a simulated crew station of a military vehicle was tested. Since crew stations (and many other applications) are inherently multi-modal, the task to have both auditory and visual stimuli was constructed. Therefore, intent was defined as the selection of a response having both an attentional context (visual or auditory) and a target goal (stimulus category). Within each attentional context, subjects had to select among three intended responses when presented with a response to the identified stimulus category. Importantly, the specific motor response (button press) was randomized on each trial, and a delay period was inserted between the stimulus presentation and the presentation of the randomized response mapping.

Figures 5A, 5B:
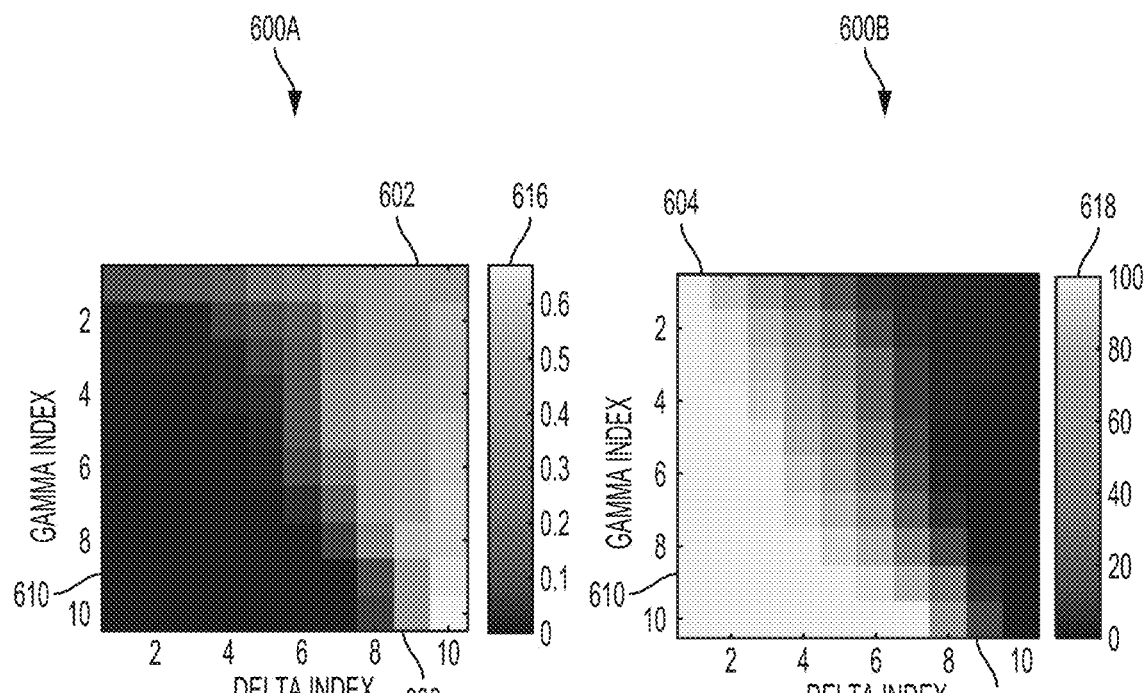
FIGS. 5A, 5B, 5C are diagrams depicting a classifier regularization process, according to one aspect of the present disclosure.
Figure 5C:
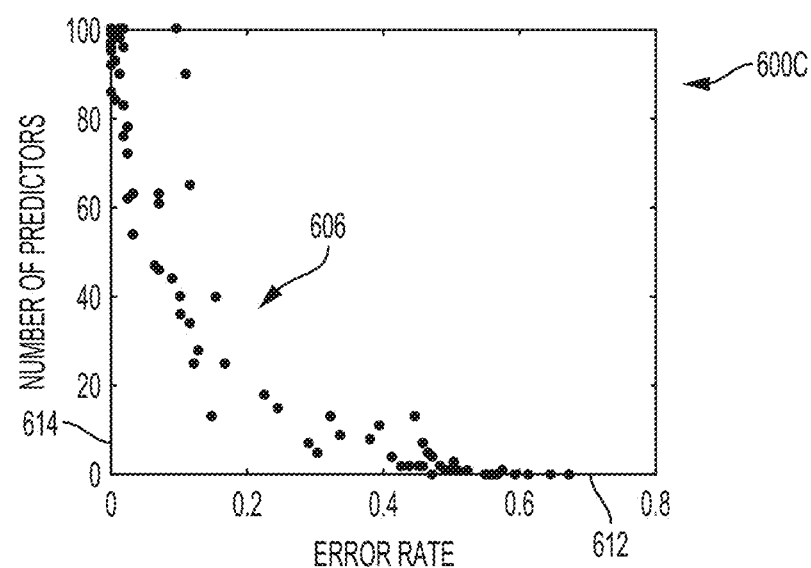

FIGS. 5A, 5B, 5C are diagrams 600A, 600B, 600C depicting a classifier regularization process, according to one aspect of the present disclosure. FIG. 5A shows a shade plot 602 of the classification error with the Delta index 608 along the x axis, the Gamma index 610 along the y axis, and a shade plot scale bar 616 shown to the right of the shade plot 602. FIG. 5B shows a shade plot 604 of the number of predictions in the model with the Delta index 608 along the x axis, the Gamma index 610 along they axis, and a shade plot scale bar 618 shown to the right of the shade plot 604. FIG. 5C is a plot 606 of the number of predictors 614, shown along the y axis, as a function of error rate 612, shown along the x axis. In various aspects, classifier regularization may refer to refining the selected bispectrum feature space corresponding to the classifier mathematical model by reducing the number of feature samples necessary as input for the classifier mathematical model. In other words, the number of samples corresponding to the determined hyper parameter values may be reduced while maintaining a predetermined level of classify 320 the context and classify 322 the goal performance of the classifier mathematical model. In some aspects, regularization may comprise determining optimal Delta and Gamma parameters of the classifier mathematical mode to minimize bispectrum feature predictors while maintaining predictive ability.

The Delta index 608 and the Gamma index 610 parameters are regularization parameters that form the x and y axes of the shade plots 600A, 600B shown in FIGS. 5A, 5B which may be used to identify and remove redundant feature predictors. The Delta index 608 and the Gamma index 610 parameters can be used to search for combinations of cross validated feature predictors that have the highest predicative ability. A suitable number of levels of Delta index 608 and Gamma index 610 parameters may be used. The discrete levels of the Delta index 608 and the Gamma index 610 parameters correspond to various combinations of cross validated feature predictors with a particular percentage of feature predictors comprising nonzero coefficients in the classifier mathematical model. A classification error or prediction rate may be calculated and plotted against the number of predictors of the discriminate analysis classifier mathematical model. Accordingly, the shade plot 606 of FIG. 5C shows the error rate 612 along the x axis and the number of predictors 614 along the y axis. The plot 606 represents the predictive quality of the various combinations of cross validated feature predictors (i.e. regularized classifiers). As can be seen in the plot 606, the error rate approaches 0 as the number of predictors approaches 100. In other words, the error rate is very low (between 0 and 0.1) when the number of feature predictors is between 50 and 100.

The shade plots 602, 604 shown in FIGS. 5A and 5B show a tradeoff between a low number of predictors and a low error rate. As previously stated, each of the shade plots 602, 604 show the Delta index 608 along the x axis and the Gamma index 610 along the y axis. Accordingly, as shown in the shade plot 602, better classification error rates (i.e., low error rates) are obtained when the Delta parameter index is low. However, as shown in the shade plot 604, a better number of predictors (i.e., a low number of predictors) are obtained when the Delta index 608 parameter index is high. In various aspects, to obtain the best classifier regularization result, the GPU processor 316 can determine the optimal combination of number of predictors and classification accuracy by iterating through the possible combinations of the Delta index 608 and the Gamma index 610 values to determine the combination of the Delta index 608 and the Gamma index 610 values corresponding to lowest error rate for a number of predictors less than or equal to a predetermined level. Therefore, the Delta index 608 and the Gamma index 610 parameters may be used to reduce the number of bispectrum feature predictors of the classifier mathematical model required to generate a hyperspace exceeding a predetermined level of predicative ability.

Tables 1-3 illustrate the results of testing the ability of the BMI to classify 320 the context and classify 322 the goal. The first column of tables 1-3 indicates an identifier of each BMI user that is a subject for testing the ability of the BMI to classify 320 the context and/or goal classify 322 the goal.

Table 1 is a chart showing performance on audio versus visual context. Table 1 is a chart depicting the performance to classify 320 the audio attentional context against the visual attentional context, according to some aspects. For Table 1, the second and third columns indicate the percentage of successful classification 320 of the context by the BMI according to the auditory and visual context classes, respectively. The fourth column of Table 1 is a class based percentage of successful classification (i.e. the average of values from the second and third columns).

TABLE 1

| Subject | Audio | Visual | Accuracy |
|---------|-------|--------|----------|
| 01OA    | 99.2% | 98.3%  | 98.7%    |
| 02OA    | 81.6% | 84.0%  | 82.9%    |

TABLE 1-continued

| Subject | Audio | Visual | Accuracy |
|---|---|---|---|
| 03OA | 95.2% | 92.2% | 93.9% |
| 04OA | 92.0% | 93.6% | 92.7% |
| 05D | 92.5% | 91.4% | 92.0% |
| 05OA | 92.0% | 85.6% | 88.7% |
| 06OA | 72.9% | 82.9% | 78.3% |
| 07OA | 92.0% | 80.0% | 86.5% |
| 08OA | 85.5% | 90.0% | 87.9% |
| 09OA | 97.0% | 96.0% | 96.6% |
| 33M | 93.4% | 85.0% | 89.3% |
| 37G | 77.2% | 84.7% | 81.1% |
| 73B | 92.3% | 96.4% | 94.5% |
| 78S | 79.2% | 87.7% | 84.5% |
| 79D | 76.3% | 83.6% | 80.2% |
| 124 | 96.3% | 98.7% | 97.5% |
| 858 | 100.0% | 98.7% | 99.5% |
| 1205 | 98.3% | 100.0% | 99.2% |
| 1206 | 96.3% | 98.2% | 97.3% |
| 1208 | 96.7% | 97.9% | 97.3% |
| 1299 | 94.5% | 96.0% | 95.3% |
| 1910 | 95.0% | 95.2% | 95.1% |
| 4394 | 97.0% | 93.8% | 95.4% |
| 4478 | 98.3% | 98.1% | 98.3% |
| Average | 91.3% | 92.0% | 91.8% |

Table 2 is a chart showing performance on visual goal states. Table 2 is a chart showing performance of the BMI to classify 322 goal states corresponding to the visual attentional context, according to some aspects. Table 2 is a chart showing performance of the BMI to classify 322 goal states corresponding to the visual attentional context, according to some aspects. For Table 2, the second through fourth columns indicate the percentage of successful goal classification 322 by the BMI according to the threat 206, a friendly 208, or a visual neutral 210 classes corresponding to identified visual stimuli, respectively. The fifth column of Table 2 is a class based percentage of successful classification (i.e. the average of values from the second through fourth columns).

TABLE 2

| Subject | Threat | Friendly | Neutral | Class-based |
|---|---|---|---|---|
| 01OA | 100.0% | 100.0% | 100.0% | 100.0% |
| 02OA | 98.9% | 97.7% | 98.9% | 98.5% |
| 03OA | 100.0% | 98.5% | 96.8% | 98.4% |
| 04OA | 98.6% | 95.9% | 98.3% | 97.5% |
| 05D | 93.2% | 97.1% | 96.9% | 95.6% |
| 05OA | 98.3% | 100.0% | 98.1% | 98.7% |
| 06OA | 100.0% | 98.5% | 100.0% | 99.5% |
| 07OA | 100.0% | 100.0% | 100.0% | 100.0% |
| 08OA | 98.5% | 98.4% | 100.0% | 99.0% |
| 09OA | 97.9% | 97.9% | 98.1% | 98.0% |
| 33M | 95.2% | 92.9% | 100.0% | 95.4% |
| 37G | 98.9% | 98.8% | 98.9% | 98.9% |
| 73B | 96.1% | 92.4% | 95.7% | 94.6% |
| 78S | 88.1% | 83.3% | 98.9% | 89.4% |
| 79D | 98.7% | 96.1% | 98.7% | 97.9% |
| 124 | 100.0% | 100.0% | 100.0% | 100.0% |
| 858 | 100.0% | 100.0% | 96.4% | 98.7% |
| 1205 | 100.0% | 97.4% | 97.5% | 98.3% |
| 1206 | 100.0% | 100.0% | 100.0% | 100.0% |
| 1208 | 100.0% | 95.1% | 100.0% | 98.5% |
| 1299 | 96.9% | 98.6% | 97.1% | 97.5% |
| 1910 | 100.0% | 100.0% | 100.0% | 100.0% |
| 4394 | 94.3% | 98.6% | 100.0% | 97.6% |
| 4478 | 100.0% | 100.0% | 100.0% | 100.0% |
| Average | 98.1% | 97.4% | 98.8% | 98.0% |

Table 3 is a chart showing performance on auditory goal states. For Table 3, the second through fourth columns indicate the percentage of successful goal classification 322 by the BMI according to the slew a gunner 218, launch a UAV 220, or treat auditory neutral 222 classes corresponding to identified auditory stimuli, respectively. The fifth column of Table 2 is also a class based percentage of successful classification (i.e. the average of values from the second through fourth columns).

TABLE 3

| Subject | Slew G | UAV | Neutral | Class-based |
|---|---|---|---|---|
| 01OA | 100.0% | 98.0% | 95.8% | 97.9% |
| 02OA | 69.0% | 72.0% | 74.0% | 71.7% |
| 03OA | 97.0% | 99.0% | 96.0% | 97.3% |
| 04OA | 86.0% | 88.0% | 89.0% | 87.7% |
| 05D | 100.0% | 98.8% | 98.9% | 99.3% |
| 05OA | 98.8% | 96.3% | 100.0% | 98.3% |
| 06OA | 97.5% | 95.1% | 96.3% | 96.3% |
| 07OA | 98.8% | 98.8% | 97.5% | 98.3% |
| 08OA | 100.0% | 97.5% | 95.0% | 97.5% |
| 09OA | 97.5% | 97.5% | 100.0% | 98.3% |
| 33M | 95.2% | 97.3% | 98.9% | 97.0% |
| 37G | 99.0% | 97.0% | 96.0% | 97.3% |
| 73B | 97.0% | 95.5% | 96.9% | 96.5% |
| 78S | 97.1% | 96.9% | 97.3% | 97.1% |
| 79D | 97.0% | 98.9% | 97.9% | 97.9% |
| 124 | 95.3% | 89.1% | 100.0% | 93.8% |
| 858 | 95.8% | 95.8% | 100.0% | 96.7% |
| 1205 | 91.7% | 95.8% | 100.0% | 95.0% |
| 1206 | 93.8% | 92.2% | 100.0% | 94.4% |
| 1208 | 84.7% | 91.7% | 100.0% | 90.6% |
| 1299 | 91.3% | 86.3% | 100.0% | 91.0% |
| 1910 | 90.6% | 90.6% | 100.0% | 92.5% |
| 4394 | 88.8% | 85.0% | 100.0% | 89.5% |
| 4478 | 87.5% | 88.9% | 100.0% | 90.6% |
| Average | 93.7% | 93.4% | 97.1% | 94.3% |

Accordingly, with reference to Tables 1-3, as previously discussed, the BMI of the disclosed system and method may directly detect the behavioral or goal related intent of a BMI user by determining the attentional context of identified stimuli and/or the intended responses of the BMI user. Tables 1-3 provide the percentages corresponding to the performance of classify 320 the context and classify 322 the goal by the BMI. In sum, for all BMI user subjects, the disclosed system and method can detect whether the user was responding to auditory stimuli or visual stimuli with an estimated 91.8% accuracy, as illustrated in Table 1. This is a significant improvement in comparison to the 50% accuracy rate corresponding to an equal probability of selecting either one of two classes. Similarly, Table 2 can provide a performance rating for the classes of response corresponding to the threat type, friend type, and neutral type stimuli, as described previously. The class based percentage values of the fifth columns of Tables 2-3 constitute the average across classification according to these stimuli types. As shown in Table 2, for all BMI user subjects, the BMI accurately detected the intended response of the BMI user for identified visual stimuli 98% of the time. As shown in Table 3, for all BMI user subjects, the BMI accurately detected the intended response of the BMI user for identified visual stimuli 94.3% of the time.

The detection of goal related signals using EEG has not been demonstrated and increases the viability of EEG as a methodology for practical BMI. The system and method for noninvasive identification of cognitive and behavioral goals can be applied to a large set of brain machine interface applications including task automation, simplifying prosthetic control, human computer interaction, and/or human augmentation (e.g., control of robotics).

Figure 6:
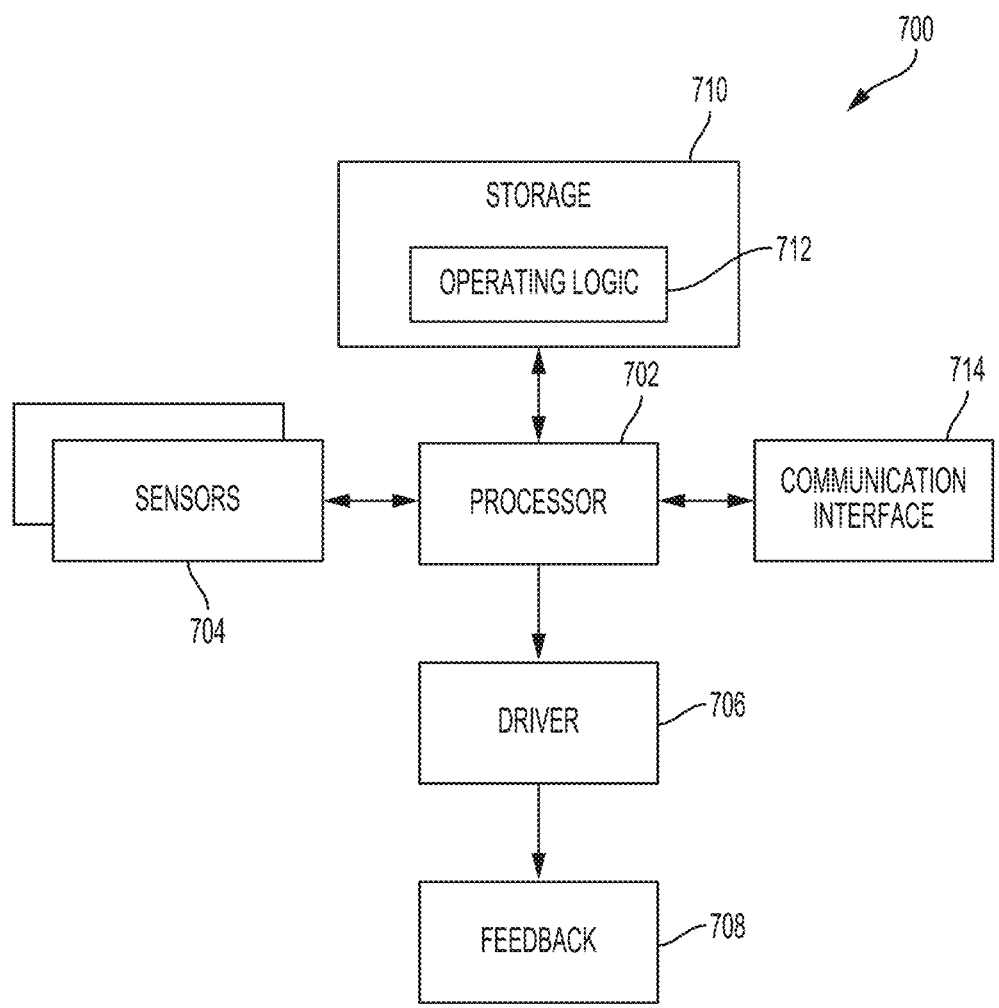
FIG. 6 illustrates an architectural or component view of a computing system 700 that may be employed to implement the system and method for noninvasive identification of cognitive and behavioral goals described in connection with FIGS. 1-5, according to one aspect of the present disclosure.

FIG. 6 illustrates an architectural or component view of a computing system 700 that may be employed to implement the system and method for noninvasive identification of cognitive and behavioral goals described in connection with FIGS. 1-5, according to one aspect of the present disclosure. In various aspects, referring also to FIG. 16, the base unit 1702 and/or the general purpose computer 1712 may comprise the computing system 700 or portions of the computing system 700 to implement the BMI in accordance with the present disclosure. The computing system 700 may comprise one or more of the GPU processor 316 or the FPGA described previously. In various aspects, as illustrated, the computing system 700 comprises one or more processors 702 (e.g., microprocessor, microcontroller) coupled to various sensors 704 (e.g., motion sensors, biometric sensors, auditory sensors, eye tracking sensors, EEG sensors) and at least one output feedback component 708 via a suitable circuit 706. For example, the output feedback component 708 may provide user intended response classification information to the BMI via a suitable circuit 706 such as a device driver 706. The one or more processors 702 may be any one of a number of single or multi-core processors known in the art. The sensors 704 can refer to, for example, the EEG device 302, eye tracking device 308, and auditory volume detector described previously. In addition, one or more storage devices 710 comprising operating logic 712 for operation is coupled to the one or more processors 702. The one or more storage devices 710 may include any suitable device such as a hard drive, random access memory (RAM), read only memory (ROM), or universal serial bus (USB) connected flash drives. The one or more storage device 710 may comprise volatile and non-volatile storage media configured to store persistent and temporal copies of the operating logic 712. The communication interface 714 may also be coupled to the one or more processors 702. In some aspects, one or more processors 702 may be packaged together with the operating logic 712 to, for example, form a System in Package (SiP) or a System on Chip (SoC). In other aspects, one or more processors 702 may be integrated on the same die with the operating logic 712.

As described earlier, the sensors 704 can comprise biometric sensors configured to detect and collect information from a BMI user such as biometric and motion data associated with position, posture, and/or movement of any part of the user's body, such as, for example, the BMI user's arms(s), hand(s), finger(s), leg(s), foot/feet, toe(s), head, neck, torso, eyes, brain waves, among other body parts. The one or more processors 702 process the biometric and motion sensor data received from the sensors 704. In some aspects, the processed data is sent to the output feedback component 708 via the driver 706 to provide feedback to the BMI. The one or more processors 702 also may be configured to execute the operating logic 712 to process the collected biometric and motion data of the BMI user, as described above. In various aspects, the operating logic 712 may be configured to provide feedback to the BMI. Therefore, the operating logic 712 may perform the initial processing, and transmit the data to a computer hosting the BMI application to determine and generate instructions on the feedback to be provided. For these aspects, the operating logic 712 may be further configured to receive the biometric, motion, and EEG data associated with the user and provide feedback to a hosting computer. In alternative aspects, the operating logic 712 may be configured to assume a larger role in receiving the biometric, motion, and EEG data and determining the feedback. Therefore, the operating logic 712 may independently determine feedback or in response to instructions from a hosting computer.

In various aspects, the operating logic 712 may be implemented in instructions supported by the instruction set architecture (ISA) of one or more processors 702, or in higher level languages that are compiled into the supported ISA. The operating logic 712 may comprise one or more logic units or modules. In various aspects, the operating logic 712 is implemented in an object oriented manner. The operating logic 712 also can be configured to be executed in a multi-tasking and/or multi-thread manner. In other aspects, the operating logic 712 may be implemented in suitable hardware such as a gate array. In some aspects, the communication interface 714 may be configured to facilitate communication between a peripheral device and the computing system 700. The communication may include transmission of the collected biometric, motion, and EEG data associated with position, posture, and/or movement data of the user's body part(s) or brain waves to a hosting computer, and transmission of data associated therewith from the hosting computer to a peripheral device. In various aspects, the communication interface 714 may be a wired or a wireless communication interface. An example of a wired communication interface may include, but is not limited to, a USB interface. An example of a wireless communication interface may include, but is not limited to, a Bluetooth interface, WiFi, among others.

Referring back to FIGS. 1 and 2, data may be collected from a predetermined number of subjects such as 15 subjects with a 32-channel active electrode EEG system 302 and an eye tracking device 304 operating at 250 Hz. In various aspects, the simulated crew station interface 100 is a suitable BMI custom software developed to collect and synchronize 310 EEG, eye tracking, simulation events, and behavioral response. For example, the custom software may be a Unity game engine for generating the 3-D environment of the simulated crew station interface 100. As previously described, in the visual context, subjects had to generate intended responses to stimuli that fell into the threat 206, a friendly 208, or visual neutral 210 categories. In the auditory context, subjects heard range callouts and generated intended responses to ranges in the low 224, mid 226, or high 228 range categories. In order to avoid trivial associations between identified stimuli and user response, each category had two different exemplary identified stimuli. Therefore, the BMI was tested to ensure that the BMI can directly determine the intended response of the BMI user based on signal processing of the collected data.

In aspects, during the BMI testing experiments, the mapping between the identified stimuli and intender user responses were randomized and delayed so that the correct button to push on the controller was only known after a delay period of at least 900 ms (0.9-1.1 s) such that BMI has sufficient time to directly determine the intender user responses. As described herein, in some aspects, non-invasive BMIs typically employ one of two control signals. The two control signals include a direct control signal for decoding moment to moment commands (e.g., when controlling a limb) and a goal-directed signal for detecting high-level intent signals in which the machine is to plan and execute the details of the detected response. The BMI of the present disclosure uses goal-directed signals to directly determine intended user response. BMIs generally focus on one modality at a time: visual, motor, or auditory. Therefore, intent is defined as the selection of one of three responses having both an attentional context (visual or auditory) and a target goal (response to stimulus category). Intent classification performance exceeded 94.3% accuracy for within both auditory and visual contexts, as shown in Tables 2-3. Intent classification for the six-class problem exceeded 80% accuracy (not shown).

Figure 7:
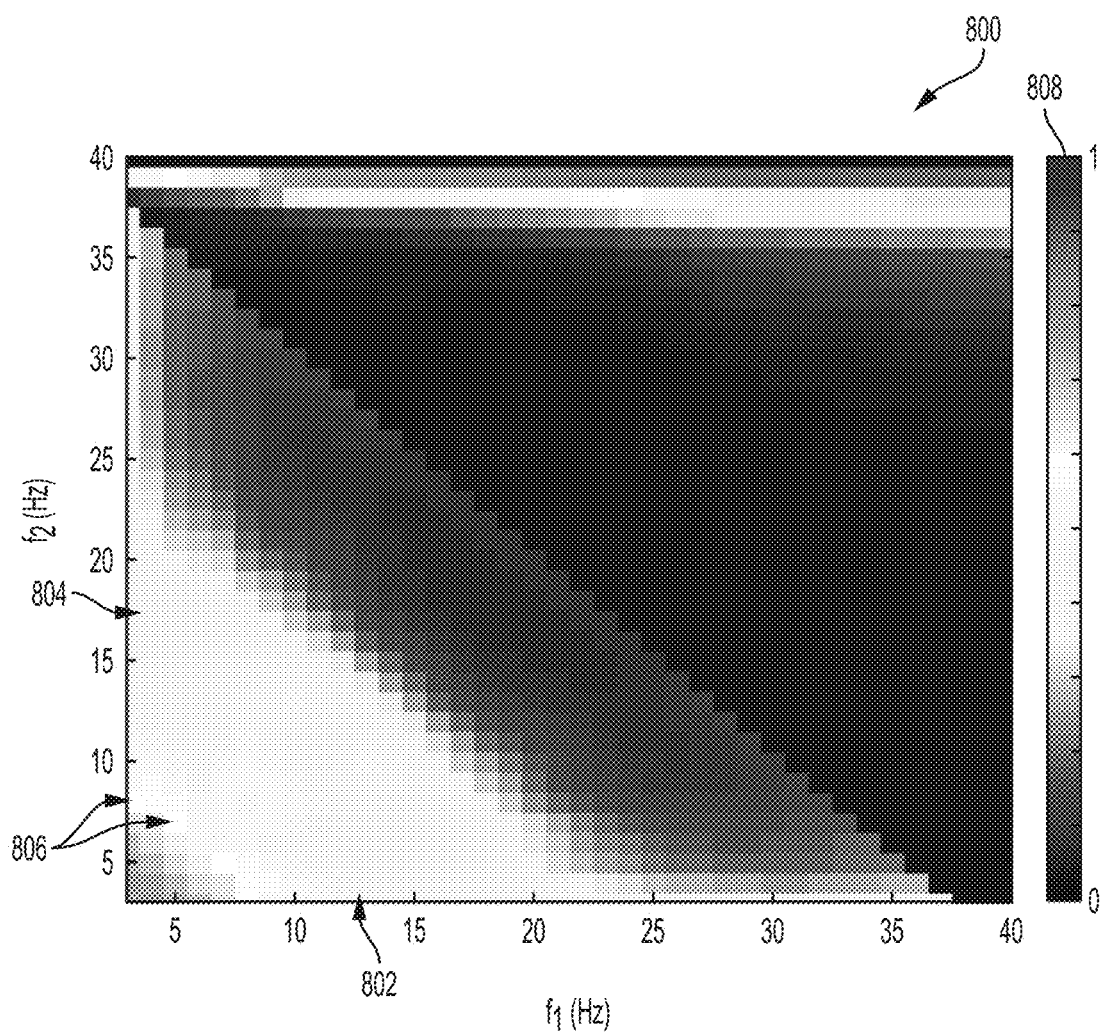
FIG. 7 shows a shade plot illustrating the high-frequency (sum region) and low-frequency (difference region) of the wavelet auto-bicoherence for EEG Channel-Pair 18-18 in a visual context and a shade plot scale bar representing feature presence to the right of the shade plot, according to one aspect of the present disclosure.

FIG. 7 shows a shade plot 800 illustrating the high-frequency (sum region) and low-frequency (difference region) of the wavelet auto-bicoherence for EEG Channel-Pair 18-18 in a visual context and a shade plot scale bar 808 representing feature presence to the right of the shade plot 800, according to one aspect of the present disclosure. Frequency $f_1$ (Hz) 802 is shown along the x axis and frequency $f_2$ (Hz) 804 is shown along the y axis. Frequency value $f_1$ along the x axis and frequency value $f_2$ along the y axis and the y axis both range from 0 to 40 Hz. As shown in FIG. 7, each of the yellow regions 806 of the shade plot 800 correspond to an auto-bicoherence (i.e., the normalized amplitude or power of the bispectrum for one particular EEG channel) value for the phase coupled two frequency values $f_1$ and $f_2$ corresponding to the x and y axes, respectively. The yellow regions 806 are represented in accordance with the shade plot scale bar 808. The auto-bicoherence value is measured based on an index ranging from 0 to 1. Various shades of the shade plot scale bar 808 correspond to numerical auto-bicoherence values between 0 and 1. In aspects, the auto-bicoherence values may indicate the degree that the normalized amplitude of the bispectrum increases or decreases. In some aspects, a yellow 806 of the shade plot 800 of FIG. 7 may correspond to a slice of the bispectrum feature space based on the yellow region 806 comprising phase correlated frequencies $f_1,f_2$ defining sum regions corresponding to frequency $f_3$ as determined based on the bi-phase of the bispectrum. Bispectrum features may appear and be extracted from sum regions.

In various aspects, the extracted bispectrum features comprise information about a set of frequencies $f_1,f_2$ within an EEG channel or between two particular EEG channels appearing within a first time bin that are phase correlated with the sum frequency $f_3$ of the set appearing within a second time bin. As previously described, selected extracted bispectrum features may be used to classify 320 the context. For example, the set of frequencies could comprise 38 Hz for $f_2$ and 5 Hz for $f_1$ such that the set of frequencies represent coupling of delta and gamma frequencies, which may indicate visual attention of the user. In particular, the change in normalized amplitude as indicated by the bi-coherence and the phase correlation as indicated by the bi-phase may be used to determine the BMI user attentional context. The nonlinear interaction of two EEG sinusoidal component frequencies corresponding to the delta and beta/gamma frequency ranges with a sum or difference frequency can indicate visual processing by the user. As previously described, a subset of the extracted bispectrum features may be selected 408 to construct a feature vector to be input into a linear discriminate classifier to classify 320 the shifts in attentional context. In various aspects, the yellow regions 806 may be determined based on calculations of the wavelet auto-bicoherence.

Figure 8:
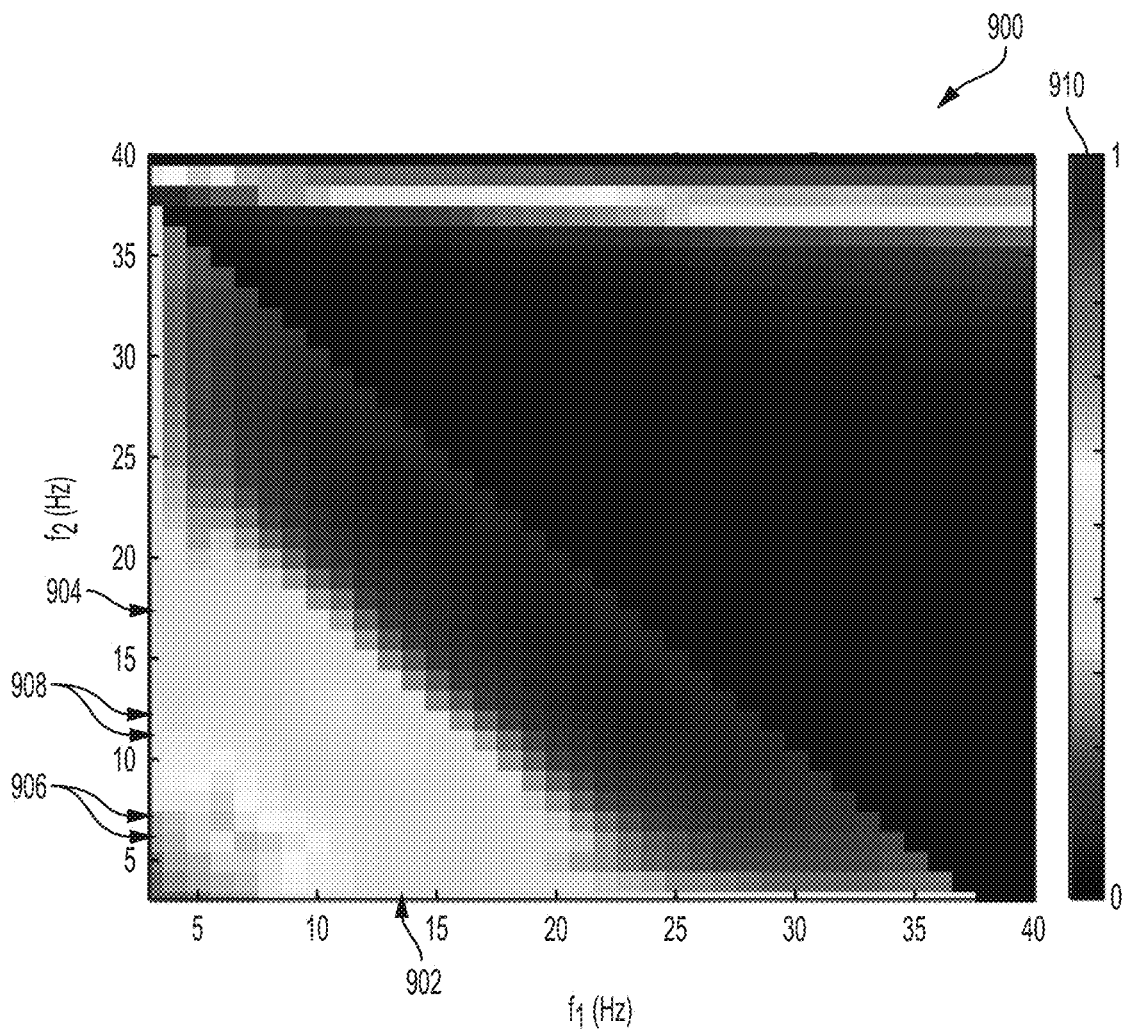
FIG. 8 shows another shade plot illustrating the high-frequency (sum region) and low-frequency (difference region) of the wavelet auto-bicoherence for EEG Channel-Pair 18-18 in an auditory context a shade plot scale bar representing feature presence to the right of the shade plot, according to aspect of the present disclosure.

FIG. 8 shows another shade plot 900 illustrating the high-frequency (sum region) and low-frequency (difference region) of the wavelet auto-bicoherence for EEG Channel-Pair 18-18 in an auditory context. A shade plot scale bar 910 represents feature presence to the right of the shade plot 900, according to aspects of the present disclosure. Similar to the shade plot 800 shown in FIG. 7, frequency $f_1$ (Hz) 902 is shown along the x axis and frequency $f_2$ (Hz) 904 is shown along the y axis. Frequency value $f_1$ along the x axis and frequency value $f_2$ along the y axis and the y axis both range from 0 to 40 Hz. Similar to the yellow region 806 (FIG. 7), regions 906, 908 of the shade plot 900 correspond to auto-bicoherence (i.e., the normalized amplitude or power of the bispectrum for one particular EEG channel) values for the phase coupled two frequency values $f_1$ and $f_2$ corresponding to the x and y axes, respectively. Various shades of the shade plot scale bar 910 correspond to numerical auto-bicoherence values between 0 and 1. In some aspects, an orange region 906 and a green region 908 of the shade plot 900 may correspond to a slice of the bispectrum feature space based on the yellow region 806 (FIG. 7) comprising phase correlated frequencies $f_1,f_2$ defining sum regions corresponding to frequency $f_3$ as determined based on the bi-phase of the bispectrum. Bispectrum features may appear and be extracted from sum regions. The orange region 906 and green region 908 are represented in accordance with the shade plot scale bar 910.

In aspects, the extracted bispectrum features comprise information about a set of frequencies $f_1,f_2$ within an EEG channel or between two particular EEG channels appearing within a first time bin that are phase correlated with the sum frequency $f_3$ of the set appearing within a second time bin. As previously described, selected extracted bispectrum features may be used to classify 320 the context. For example, the set of frequencies could represent phase correlation or coupling that may indicate auditory attention of the user (e.g., the delta and gamma or some other combination of frequencies). In particular, the change in normalized amplitude as indicated by the bi-coherence and the phase correlation as indicated by the bi-phase may be used to determine the BMI user attentional context. The nonlinear interaction of two EEG sinusoidal component frequencies corresponding to the delta and beta/gamma frequency ranges with a sum or difference frequency can indicate visual processing by the user. As previously described, a subset of the extracted bispectrum features may be selected 408 to construct a feature vector to be input into a linear discriminate classifier to classify 320 the shifts in attentional context. In various aspects, the orange region 906 and the green region 908 may be determined based on calculations of the wavelet auto-bicoherence.

Figure 9:
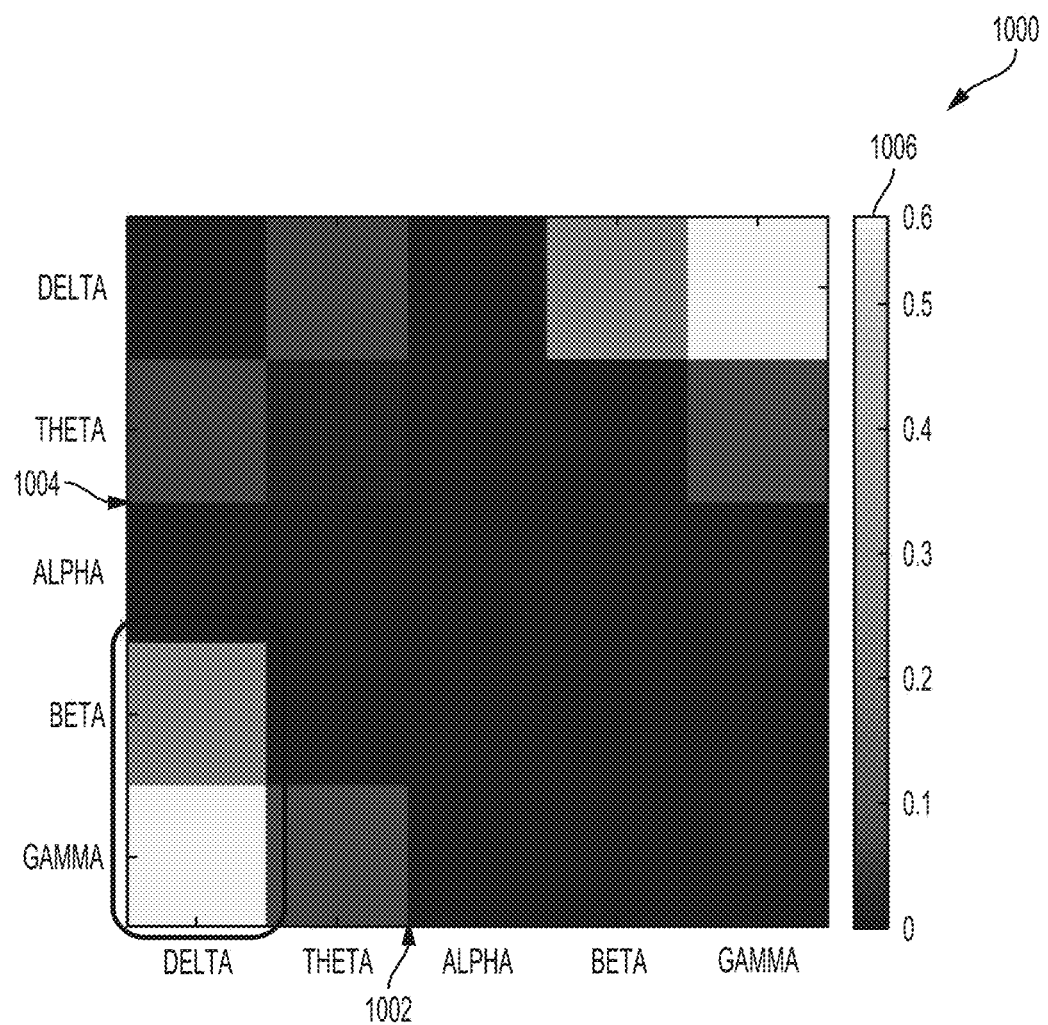
FIG. 9 shows a shade plot analyzing the distribution of bi-spectral phase features across multiple user subjects to classify the context (i.e., context discrimination) and a shade plot scale bar representing the probability to the right of the shade plot, according to one aspect of the present disclosure.

FIG. 9 shows a shade plot 1000 analyzing the distribution of bi-spectral phase features across multiple user subjects to classify 320 the context (i.e., context discrimination) and a shade plot scale bar 1006 representing the probability to the right of the shade plot 1000, according to one aspect of the present disclosure. The graph 1000 depicts a probability distribution of sets of phase coupled frequencies of bi-spectral features for the entire feature space, that are distributed based on five bands of frequencies. In some aspects, the x axis 1002 and y axis 1004 each indicate the five bands of frequencies (Delta, Theta, Alpha, Beta, Gamma). As previously described, the five bands are delta: 1-4 Hz, theta: 4-8 Hz, alpha 8-14 Hz, beta: 13-30 Hz, and gamma: 30-40 Hz frequency bands. It is well known that delta-beta and delta-gamma frequency band coupling corresponds to visual attention and/or auditory attention (Romero et al., 2015; Lakatos et al., 2008). The probability shade plot scale bar 1006 is indexed based on various shades that correspond to a range from 0 to 0.6. For example, as indicated on the graph 1000, features involving delta-gamma frequency band coupling account for approximately 60% of the feature space while features involving delta-beta frequency band coupling account for approximately 25% of the feature space. Therefore, approximately 85% or more of the features involve coupling of delta to beta and gamma frequencies. In addition, examination of the spatial distribution of EEG channel pairs also shows that the majority of features tend to be for cross-frequency coupling on the same EEG channel (not shown). This result is in agreement with published findings which have shown delta-beta and delta-gamma coupling during user attention.

Figure 10:
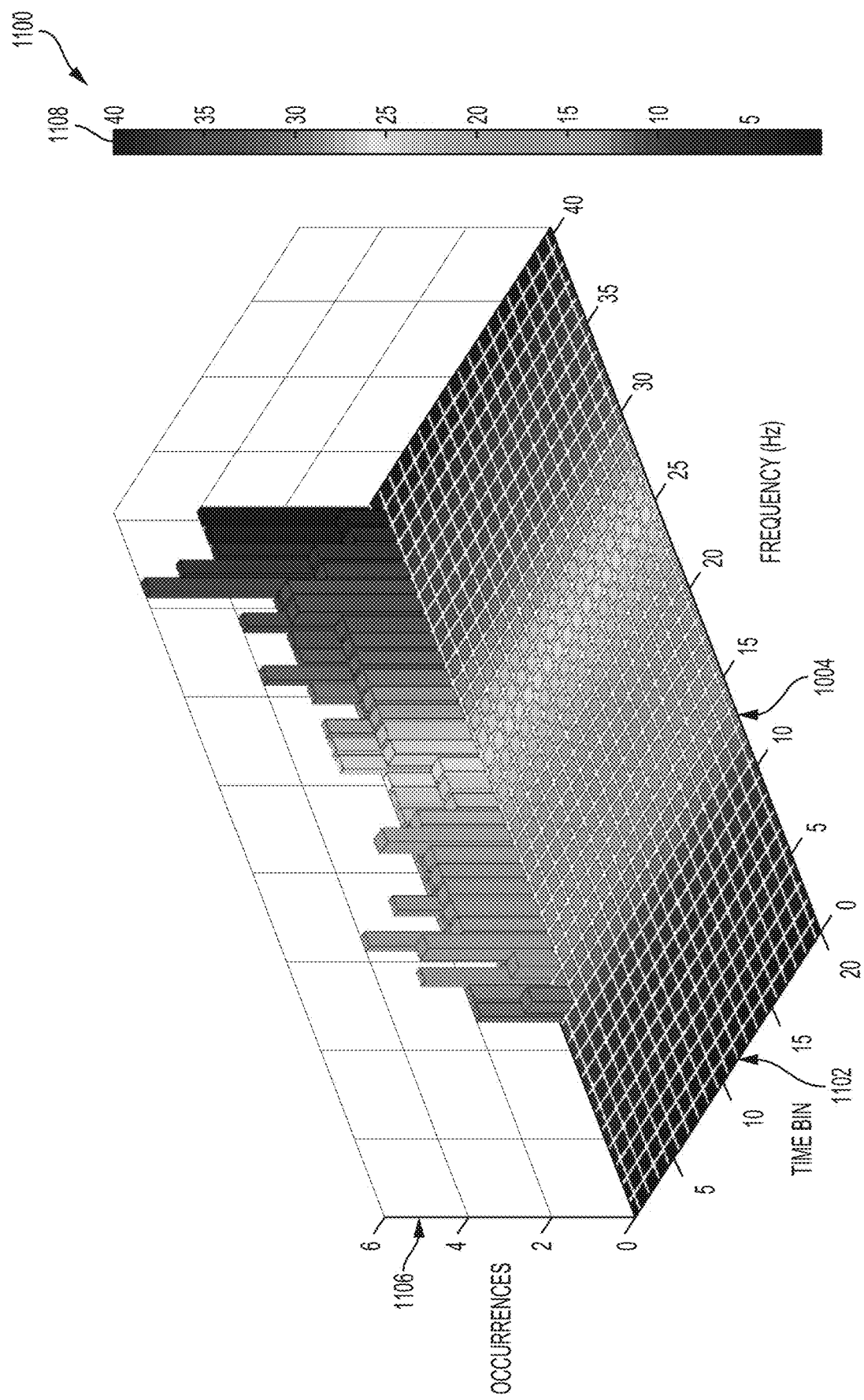
FIG. 10 shows a graph analyzing the distribution of bi-spectral phase features across BMI user subjects to classify the context, according to one aspect of the present disclosure.

FIG. 10 shows a graph 1100 analyzing the distribution of bi-spectral phase features across BMI user subjects to classify 320 the context, according to one aspect of the present disclosure. Frequency (Hz) 1104 ranging from 0-40 Hz is shown along the x axis, time bin 1102 indexes ranging from 0 to 20 is shown along the y axis, and occurrences 1106 ranging from 0-6 is shown along the z axis. In some aspects, the time bins may be incremented by a suitable value, such as 100 ms. Various shades of the spectrum axis 1108 correspond to numerical values between 0 and 40. In various aspects, bi-spectral features are primarily selected in early time bins, suggesting the ability of the BMI to rapidly separate between the visual and auditory attentional contexts. As previously described, in some aspects, features may be selected based on a training set process.

Figure 11:
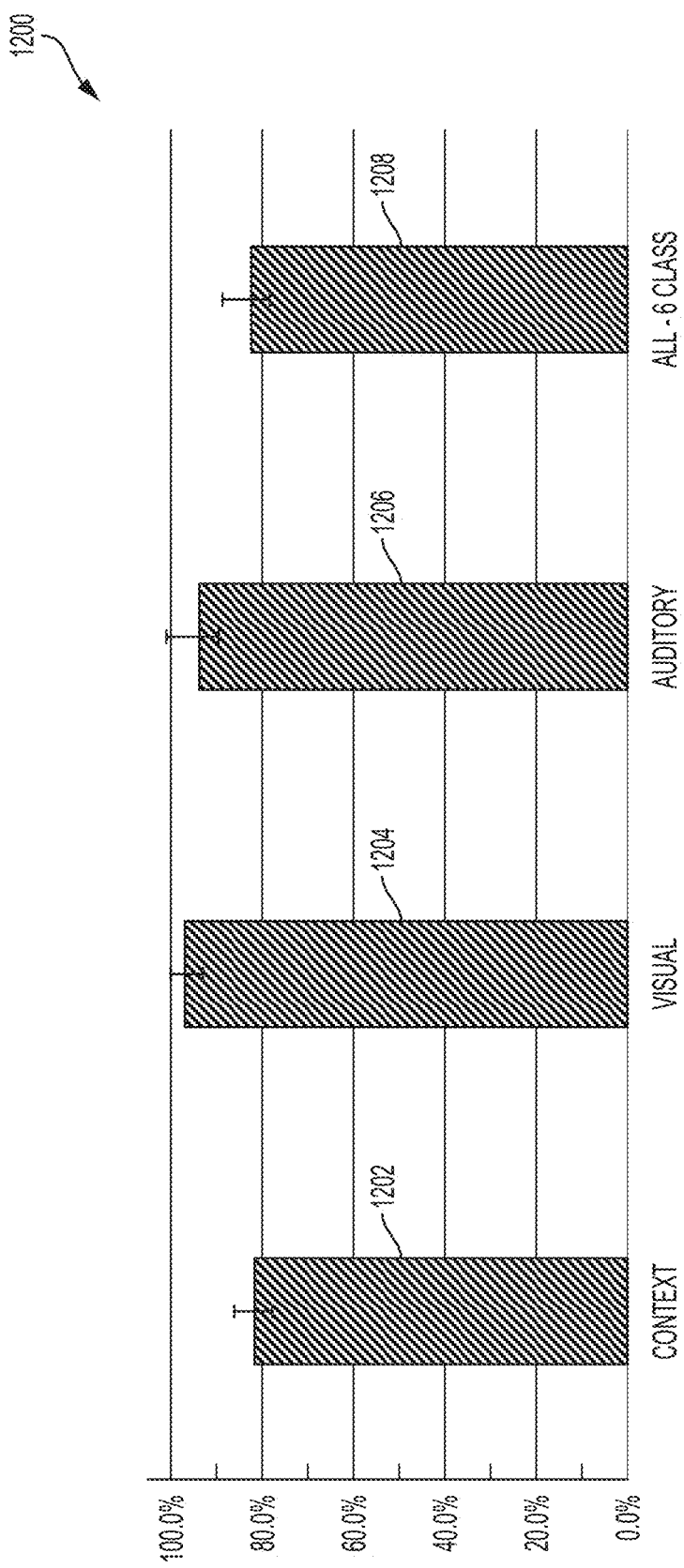
FIG. 11 shows a chart of the BMI classification performance over the course of trials across 15 user subjects for combined visual and auditory attentional context, visual attentional context, auditory attentional context, and all six visual and auditory user response classes combined, according to one aspect of the present disclosure.

FIG. 11 shows a chart 1200 of the BMI classification performance over the course of trials across 15 user subjects for combined visual and auditory attentional context 1202, visual attentional context 1204, auditory attentional context 1206, and all six visual and auditory user response classes 1208 combined, according to one aspect of the present disclosure. The classification performance is measured based on mean plus or minus standard deviation. As shown in the chart 1200, the context 1202 classification has a mean of approximately 81% with a standard deviation of approximately 3%. In various aspects, the combined visual and auditory attentional context 1202 classification comprises the BMI to classify 320 the context between the visual and auditory attentional contexts (i.e., identify whether the user identified stimulus is visual or auditory) for BMI users that perceive the appearance of and/or a shift in both visual and auditory stimuli over the course of one or more trials. As previously described in connection with FIG. 2, the six user response classes 1208 comprise threat 206, friendly 208, or visual neutral 210 for the visual attentional context and slew a gunner 218, launch a UAV 220, or treat auditory neutral 222 for the auditory attentional context. The visual attentional context 1204 classification comprises the BMI to classify 322 the goal between the threat 206, friendly 208, or visual neutral 210 classes for BMI users that perceive the appearance of and/or a shift in visual stimuli. The visual attentional context 1204 classification has a mean of approximately 97% with a standard deviation of approximately 2%. The auditory attentional context 1206 classification comprises the BMI to classify 322 the goal between slew a gunner 218, launch a UAV 220, or treat auditory neutral 222 classes for BMI users that perceive only the appearance of and/or a shift in auditory stimuli. As shown in the chart 1200, the auditory 1206 classification has a mean of approximately 94% with a standard deviation of approximately 6%. As shown in the chart 1200, the six 1208 combined class classification has a mean of approximately 82% with a standard deviation of approximately 2%. The six 1208 combined class classification comprises the BMI to classify 322 the goal between threat 206, a friendly 208, visual neutral 210, slew a gunner 218, launch a UAV 220, and treat auditory neutral 222 classes for BMI users that perceive the appearance of and/or a shift in both visual and auditory stimuli.

Figure 12:
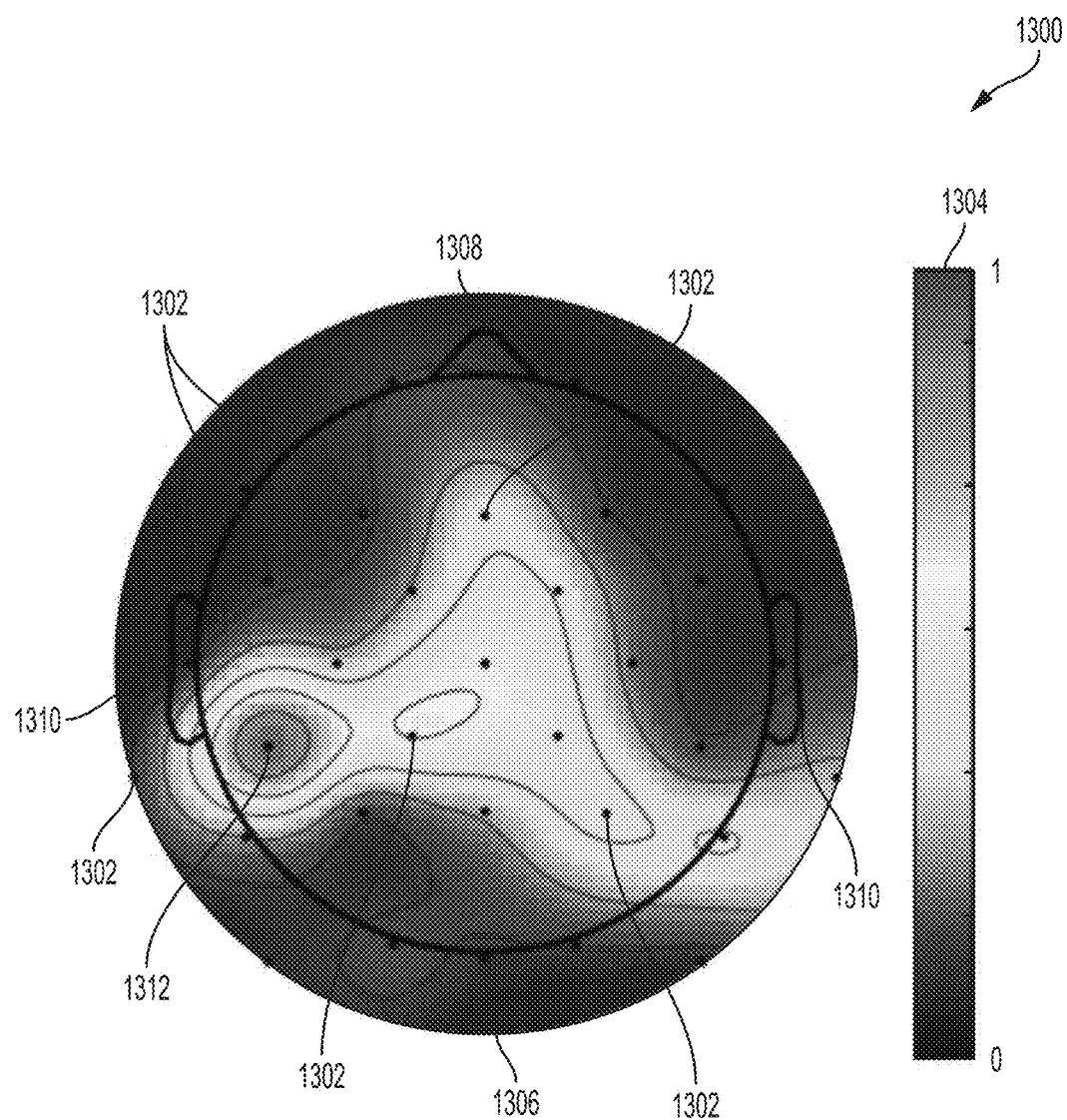
FIG. 12 shows an EEG shade plot representing a brain map illustrating the spatial distribution of delta-beta and delta-gamma frequency coupling bi-spectral features across subjects for context discrimination and a shade plot scale bar representing feature presence to the right of the EEG shade plot, according to one aspect of the present disclosure.

FIG. 12 shows a EEG shade plot 1300 representing a brain map illustrating the spatial distribution of delta-beta and delta-gamma frequency coupling bi-spectral features across subjects for context discrimination and a shade plot scale bar 1304 representing feature presence to the right of the EEG shade plot 1300, according to one aspect of the present disclosure. The shade plot 1300 may comprise EEG electrodes 1302 disposed along the head 1306 of an EEG user according to a 10 by 10 electrode layout. The head 1306 of the user is shown in top view with nose 1308 and ears 1310 to provide left/right orientation context. As previously described, each of the EEG electrodes 1302 correspond to an EEG channel. Values displayed at each electrode site represent the percentage of features involving that channel (normalized to the electrode with the maximum number of features). The shade plot 1300 shows that the features used for context discrimination exhibit a strong bias to parietal and centroparietal channels with a preference for the left hemisphere 1312. Previous work has shown coherence in the delta and beta/gamma frequencies in these locations related to visual attention. The strong left hemispheric 1312 bias also may be related to the language processing demands of human tasks. The shade plot scale bar 1304 is indexed based on various shades that correspond to a range from 0 to 1. The range between 0 to 1 corresponds to a percentage of bispectral features associated with each particular EEG channel 1302. For each EEG channel 1302, the color indicates the percentage of associated features.

Figure 13:
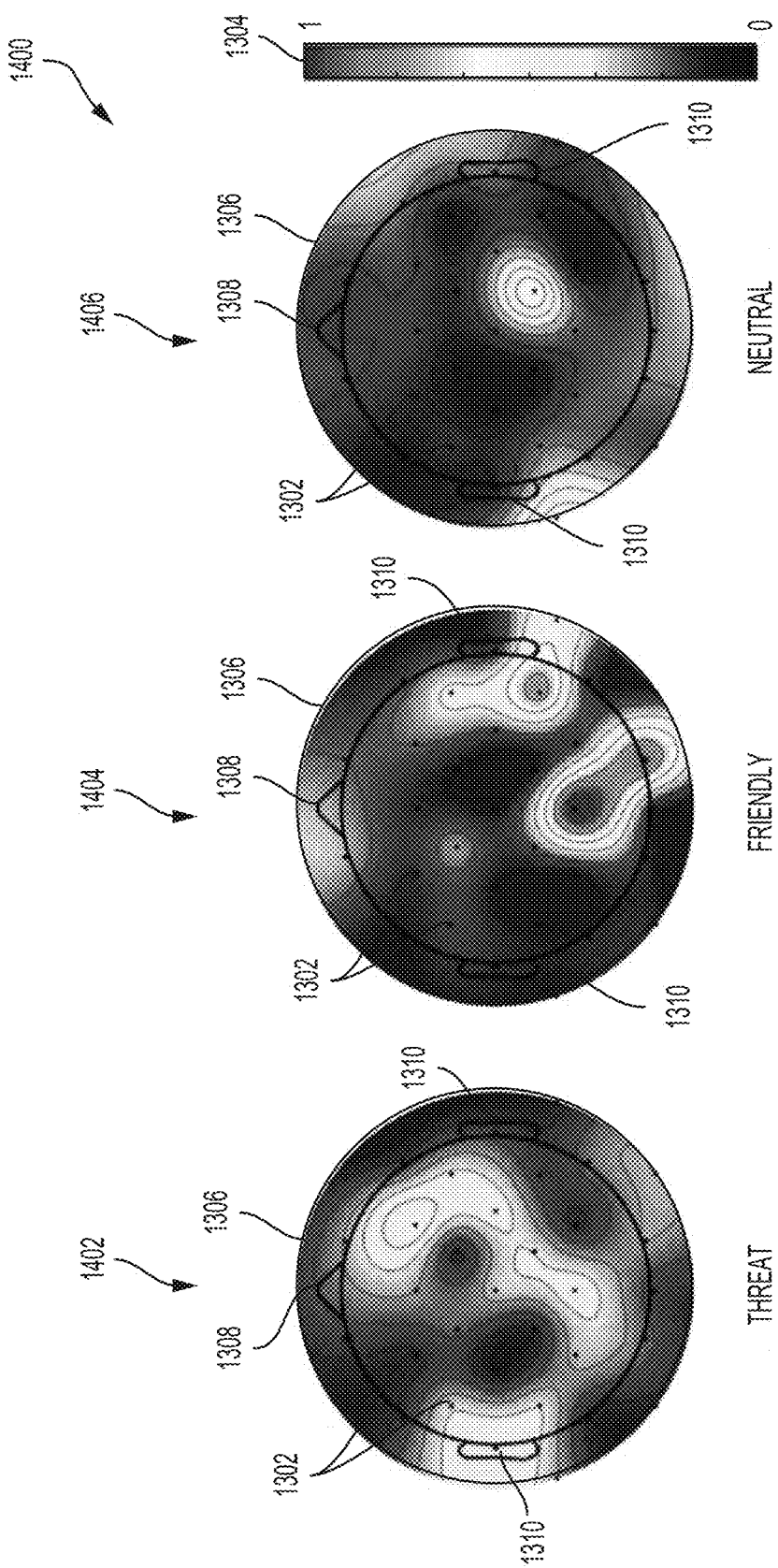
FIG. 13 shows additional EEG shade plots representing EEG brain maps comprising a threat EEG brain map, a friendly EEG brain map, and a neutral EEG brain map and a shade plot scale bar representing feature presence to the right of the EEG shade plots, according to one aspect of the present disclosure.

FIG. 13 shows additional EEG shade plots 1400 representing EEG brain maps comprising a threat EEG brain map 1402, a friendly EEG brain map 1404, and a neutral EEG brain map 1406 and a shade plot scale bar 1304 representing feature presence to the right of the EEG shade plots 1400, according to one aspect of the present disclosure. The EEG brain maps 1402, 1404, 1406 correspond to the threat 206, friendly 208, and visual neutral 210 classes for the visual attentional context, as described in connection with FIG. 2. The shade plot scale bar 1304 shown in FIG. 13 also appears in FIG. 14. The EEG brain maps 1402, 1404, 1406 show the spatial distribution of delta-beta/gamma frequency coupling features across subjects for visual goal discrimination. While highly distributed, the features do involve areas involved with visuospatial processing. The threat EEG brain map 1402 depicts relative high percentages of features associated with the EEG channels T7, F4, C4, PZ, etc. These EEG channels correspond to various portions of the brain. The friendly EEG brain map 1404 depicts relative high percentages of features associated with the EEG channels PZ, O2, CP6, FC6. The neutral EEG brain map 1406 depicts relative high percentages of features associated with the EEG channels CP2, C4, P2, P4.

Figure 14:
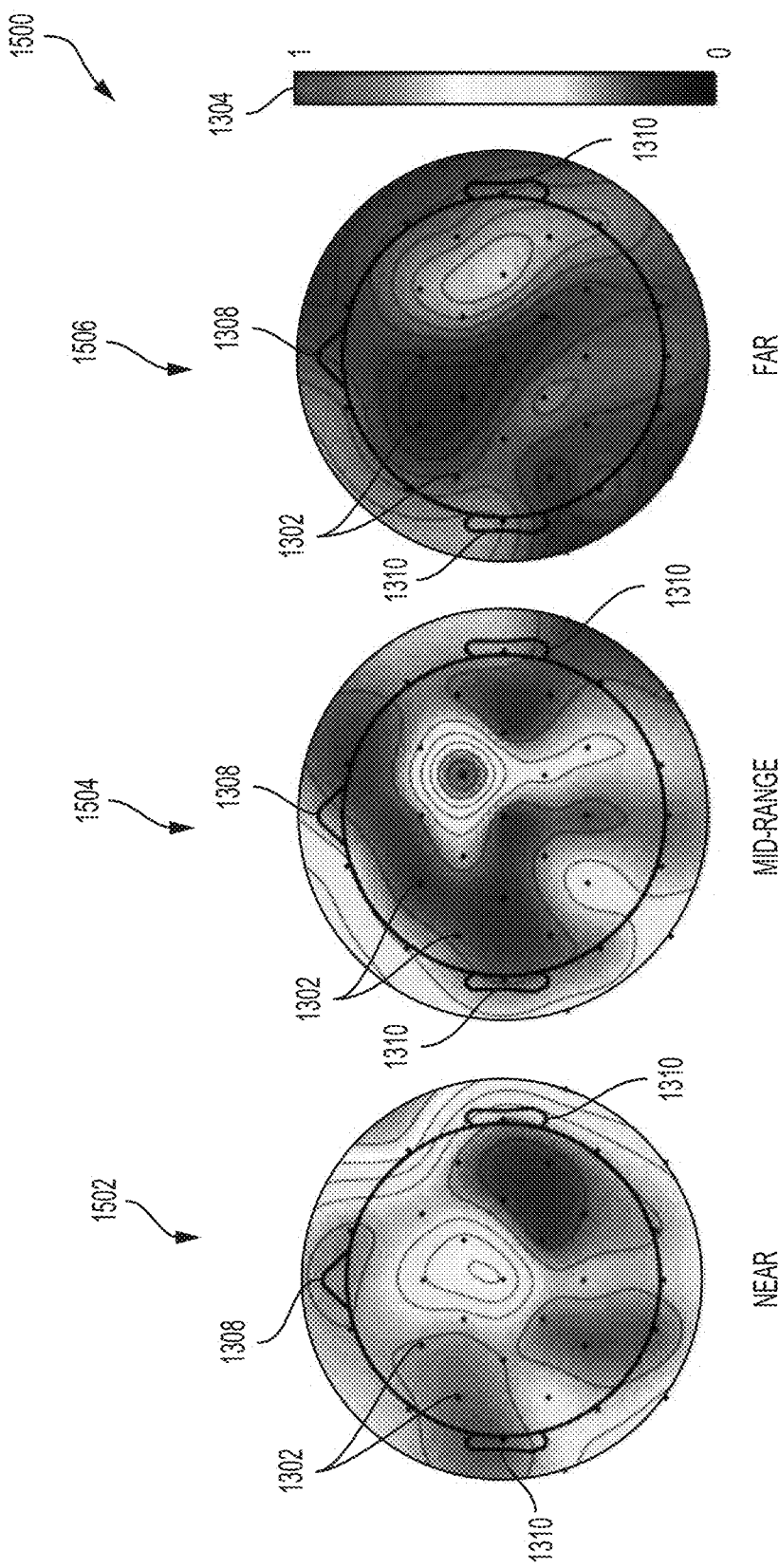
FIG. 14 shows additional EEG shade plots representing EEG brain maps comprising a near range EEG brain map, a mid range EEG brain map, and far range EEG brain map and a shade plot scale bar representing feature presence to the right of the EEG shade plots, according to one aspect of the present disclosure.

FIG. 14 shows additional EEG shade plots 1500 representing EEG brain maps 1500 comprising a near range EEG brain map 1502, a mid range EEG brain map 1504, and far EEG brain map 1506 and a shade plot scale bar 1304 representing feature presence to the right of the EEG shade plots 1400, according to one aspect of the present disclosure. The EEG brain maps 1502, 1504, 1506 correspond to the low 224, mid 226, or high 228 range classes for the auditory attentional context as described in connection with FIG. 2. The shade plot scale bar 1304 representing feature presence shown in FIG. 12 also appears in FIG. 14. The EEG brain maps 1502, 1504, 1506 show the spatial distribution of delta-beta/gamma frequency coupling features across subjects for auditory goal discrimination. Features generally cluster around frontal and fronto-central electrodes. This clustering may reflect the documented involvement of premotor cortical regions in linguistic representations of proximity. The near range EEG brain map 1502 depicts relative high percentages of features associated with the EEG channels FCz, Fz, F8, etc. These EEG channels correspond to various portions of the brain. The midrange EEG brain map 1504 depicts relative high percentages of features associated with the EEG channels FC4, F4, FC2, C4, FC6. The far range EEG brain map 1506 depicts relative high percentages of features associated with the EEG channels are F4, C4, CP6.

Figure 15A:
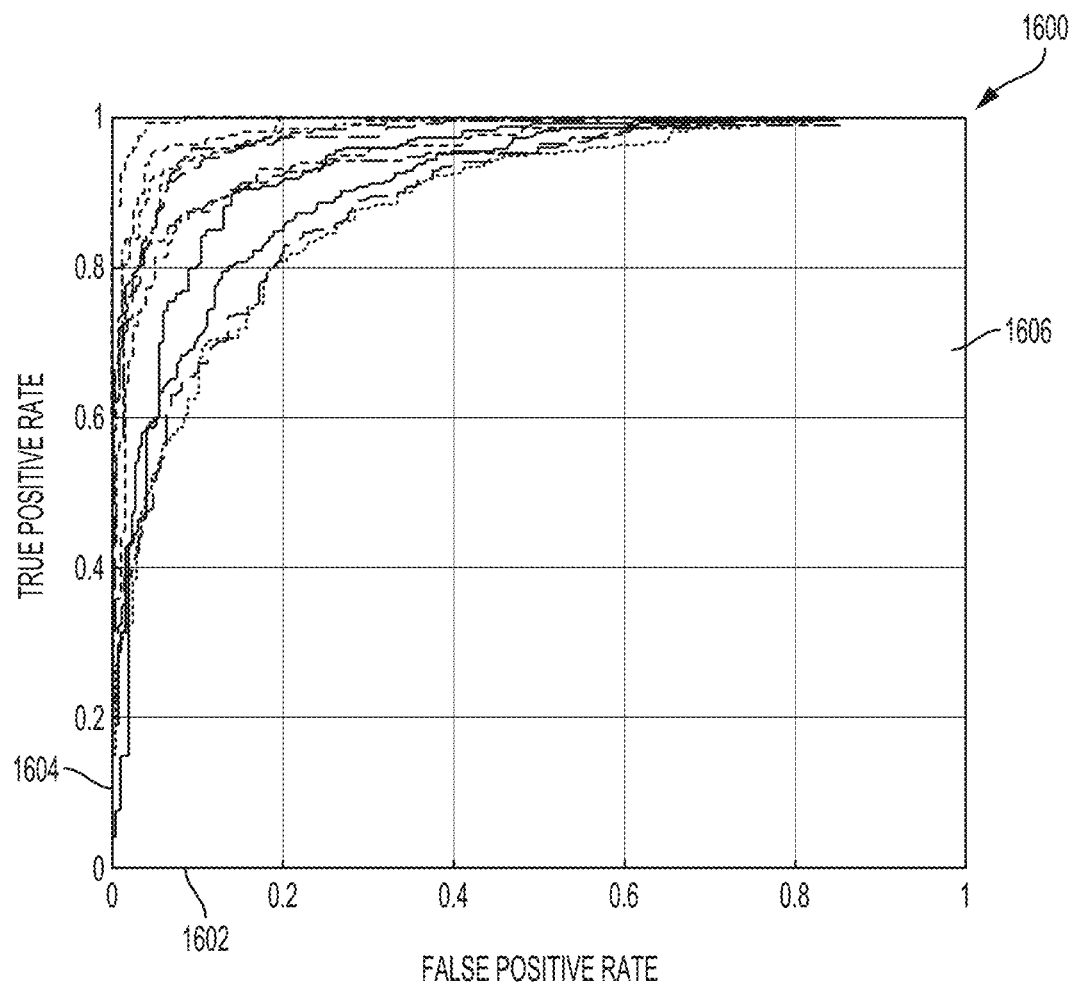
FIGS. 15A-15D show receiver operating characteristic (ROC) curves for (a) Context (b) Visual (c) Auditory and (d) 6-class classification for the linear discriminate classifier across 15 subjects, according to one aspect of the present disclosure.
Figure 15B:
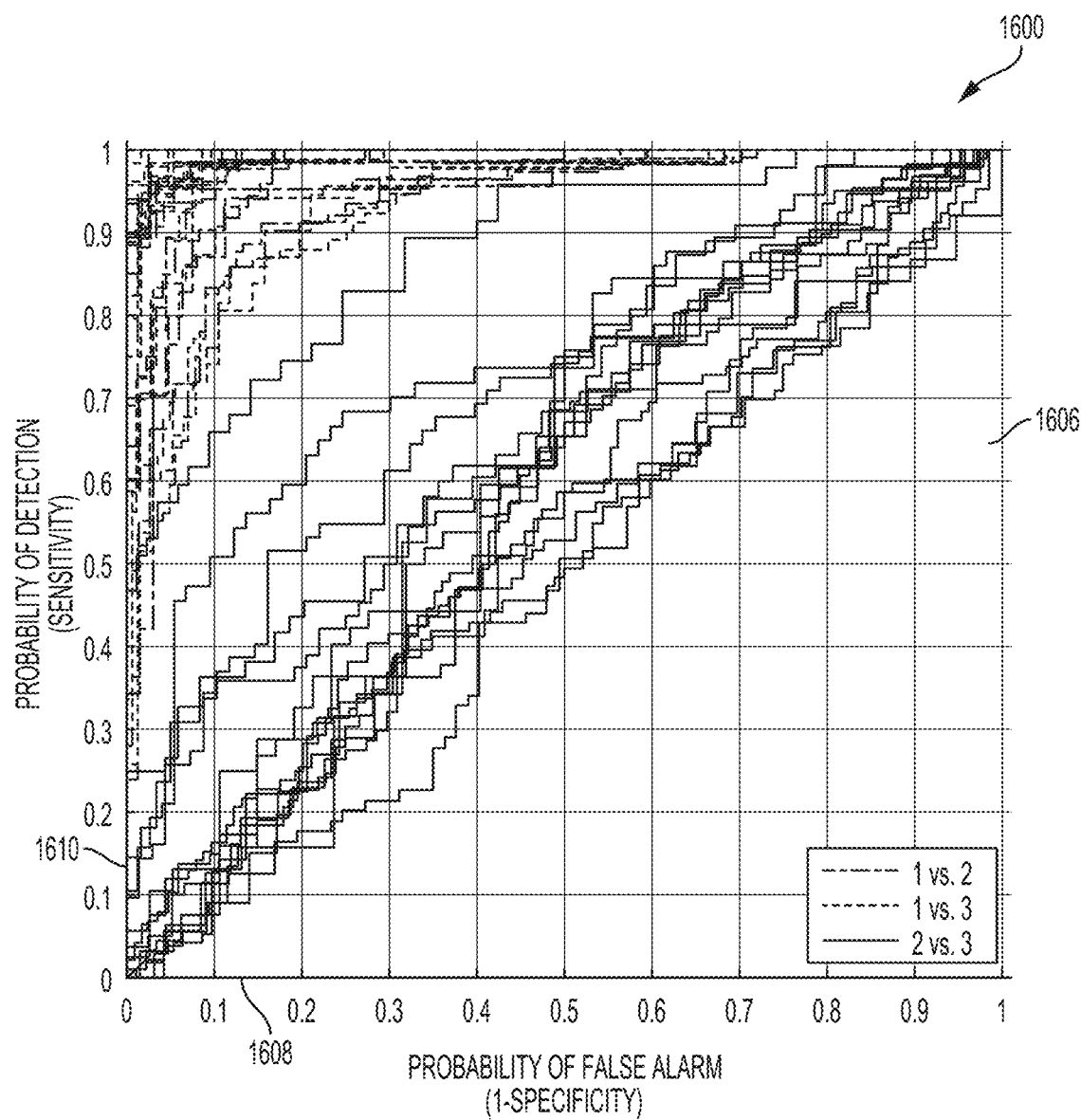
Figure 15C:
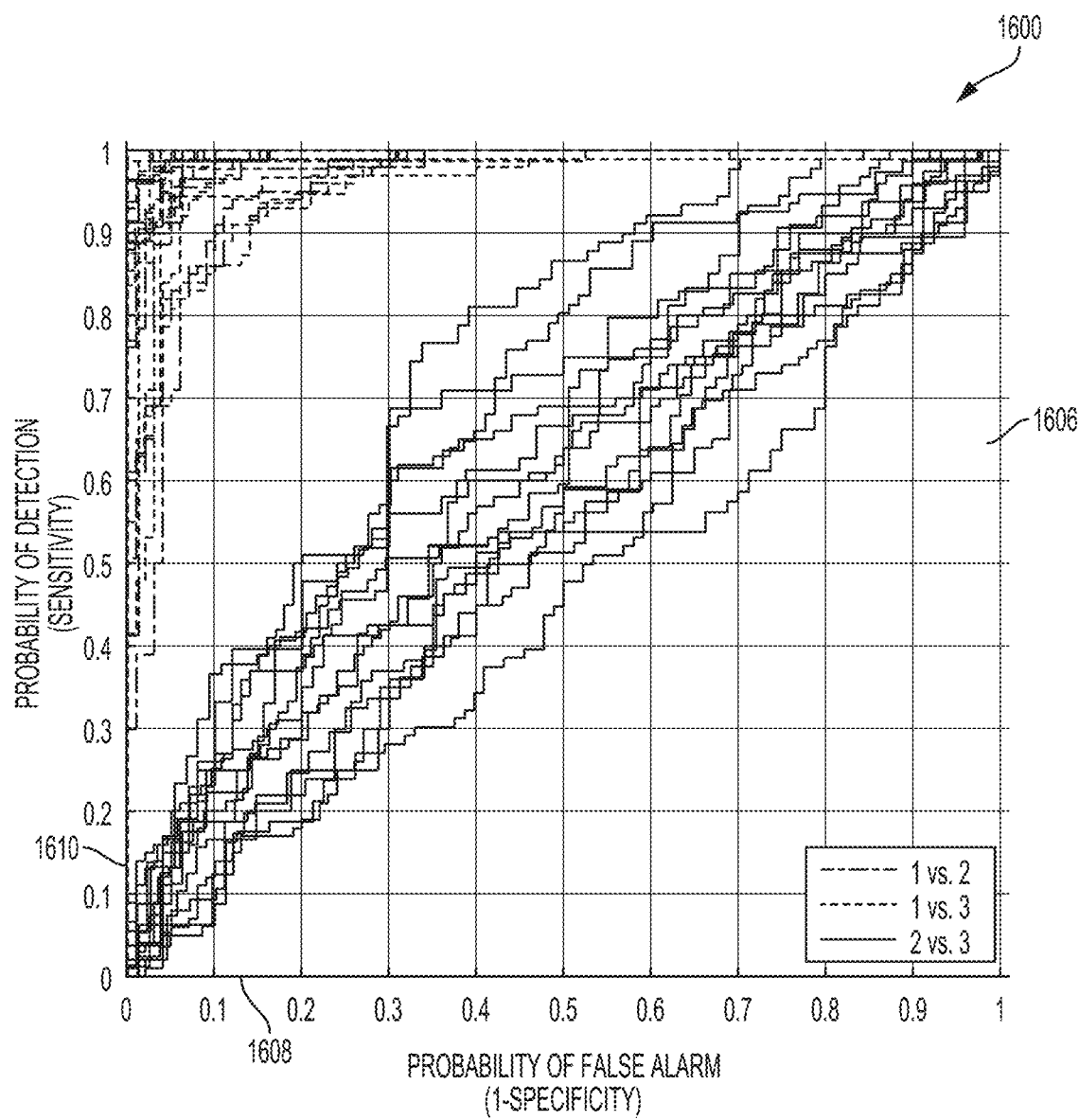
Figure 15D:
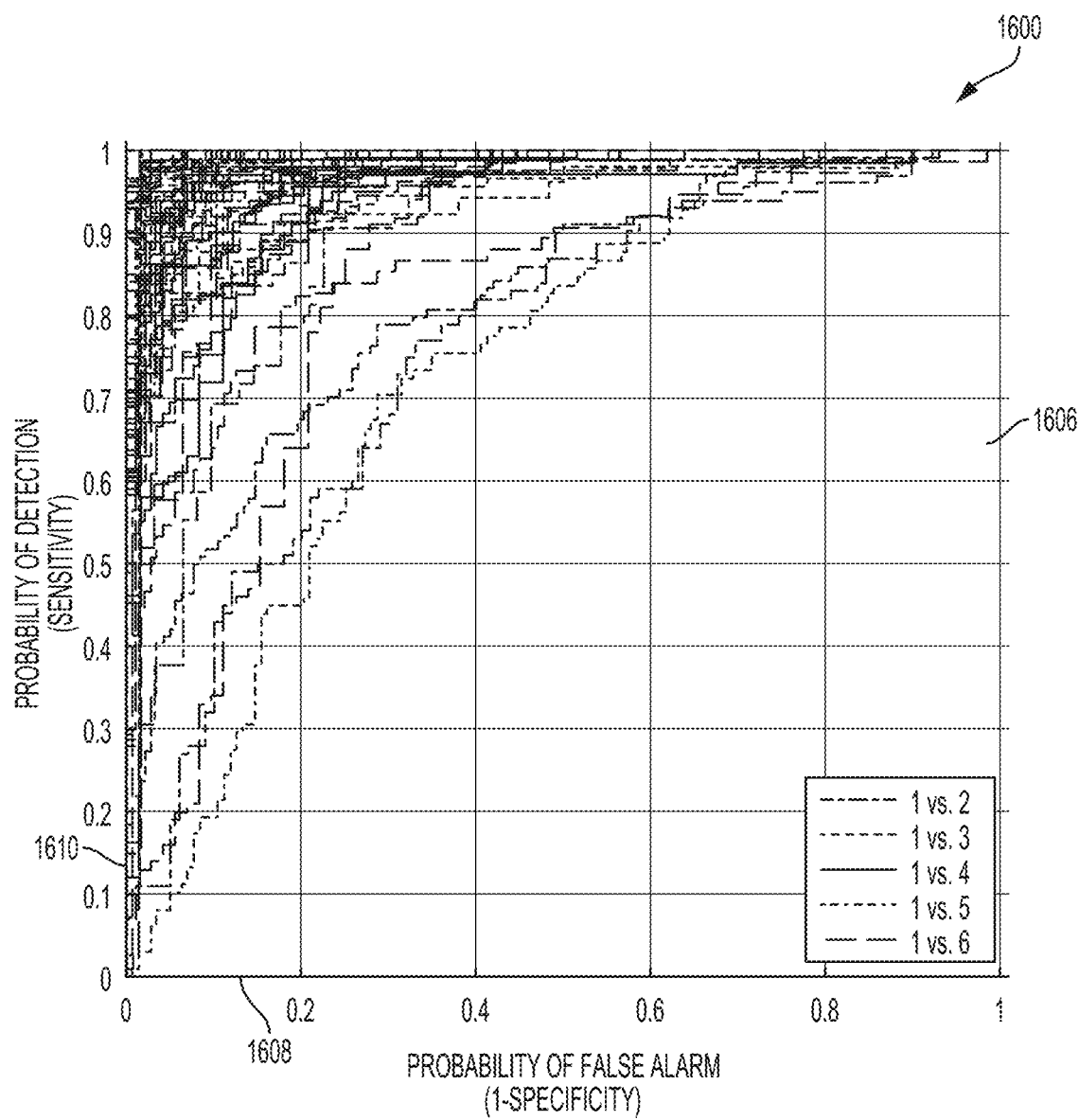

FIGS. 15A-15D show receiver operating characteristic (ROC) curves 1600 for (a) Context (b) Visual (c) Auditory and (d) 6-class classification for the linear discriminate classifier across all 15 subjects, according to one aspect of the present disclosure. The ROC curves 1600 provide a graphic depiction of the tradeoff between the sensitivity and specificity of a hyperplane generated by the linear discriminate classifier. In other words, the sensitivity of the linear discriminate classifier to alert the BMI that context classification 320 or goal classification 322, as described in connection FIG. 3, has occurred, varies inversely with the ability of the linear discriminate classifier to specifically identify the features that indicate an accurate context classification 320 or goal classification 322 has occurred. Therefore, sensitivity may be measured by a true positive rate and specificity may be measured by a false positive rate. In FIG. 15A, the x axis denotes and indexes false positive rate 1602 ranging from 0 to 1 in denoted increments of 0.2. They axis denotes and indexes true positive rate 1604 ranging from 0 to 1 in denoted increments of 0.2. In FIGS. 15B-15D, the x axis denotes and indexes false alarm probability 1608 (i.e., 1 minus specificity) ranging from 0 to 1 in denoted increments of 0.1. The y axis denotes and indexes detection probability 1610 (i.e., sensitivity) ranging from 0 to 1 in denoted increments of 0.1. For the visual and auditory intent classification, the area under the curve (AUCs) 1606 is consistently higher for Threat vs. others and Near vs. others contrasts.

Figure 17:
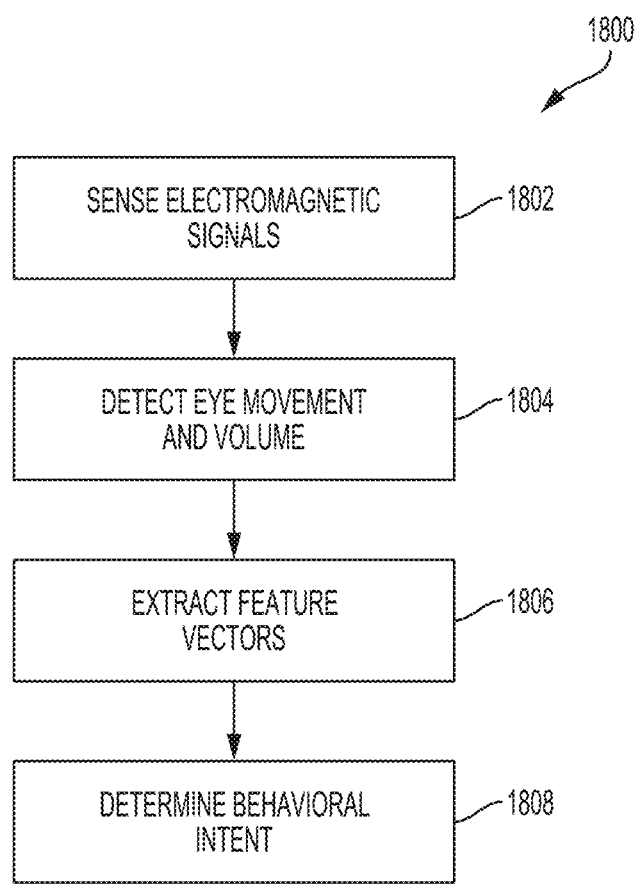
FIG. 17 is a logic diagram of a method for identifying a behavioral intent of a person, according to one aspect of the present disclosure.

FIG. 17 is a logic diagram 1800 of a method for identifying a behavioral intent of a person, according to one aspect of the present disclosure. The method may be executed in a hardware environment disclosed in connection with FIGS. 3, 6, and 16. According to the method, an electroencephalogram attached to a person senses 1802 electromagnetic signals generated by the brain of the person, wherein the electromagnetic signals comprise a time component and a frequency component. A monitor detects 1804 an eye movement of the person and a volume of an auditory stimulus, wherein the eye movement corresponds to a visual stimulus. A processor extracts 1806 a first set of feature vectors corresponding to the visual stimulus and a second set of feature vectors corresponding to the auditory stimulus, wherein each of the feature vectors define a class of behavioral intent. The processor determines 1808, by the processor, a behavioral intent of the person based on the first set of feature vectors and the second set of feature vectors.

Figure 18:
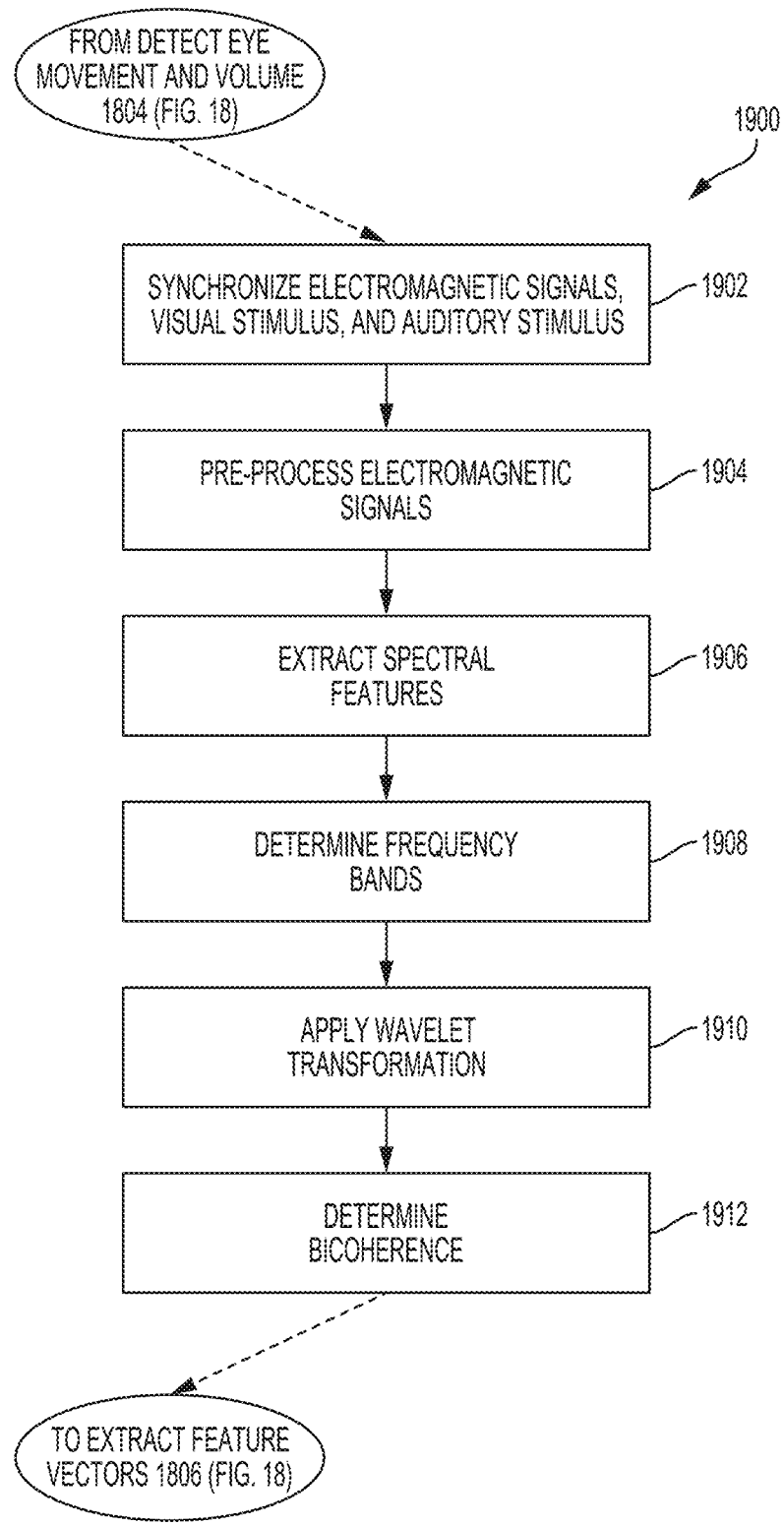
FIG. 18 is a logic diagram illustrating additional elements of a method for identifying a behavioral intent of a person, according to one aspect of the present disclosure.

FIG. 18 is a logic diagram 1900 illustrating additional elements of a method for identifying a behavioral intent of a person, according to one aspect of the present disclosure. The method may be executed in a hardware environment disclosed in connection with FIGS. 3, 7, and 17. In one aspect, additional functions of the processor, after the monitor detects 1804 an eye movement of the person and a volume of an auditory stimulus, include that the processor synchronizes 1902 the electromagnetic signals with the visual stimulus and the auditory stimulus. In yet another aspect, the processor pre-processes 1904 the electromagnetic signals, wherein the pre-processing comprises filtering and referencing the electromagnetic signals; and extracting 1906, by the processor, spectral features from the electromagnetic signals. The processor also may determine 1908 a first frequency band and a second frequency band of the spectral features. The processor may apply 1910 a wavelet transformation to the electromagnetic signals, wherein the wavelet transformation is applied over a period of time corresponding to the time component; and determine 1912 a bicoherence element to define a measure of phase coupling based on the first frequency band and the second frequency band, wherein the measure of phase coupling corresponds to the first set and the second set of the feature vectors. In yet another aspect, the first set and the second set of feature vectors may be extracted 1806 based on the measure of phase coupling.

The present disclosure has demonstrated the ability to classify intended responses to auditory and visual stimuli, such as in a multimodal simulation of an army vehicle crew station. Classification of intended responses in both auditory and visual goal conditions exceeded 94% accuracy. The most useful bifrequency features were in the Delta-Gamma and Delta-Beta range. This is consistent with extant literature on allocation of attention. The spatial distribution of the features was consistent with known functional anatomy of multi-modal, visual, and auditory processing. These results suggest that higher order spectral (HOS) analysis can be useful in developing BMI systems and expanding the capabilities of non-invasive systems beyond binary classification and motor decoding.

While various details have been set forth in the foregoing description, it will be appreciated that the various aspects of the system and method for noninvasive identification of cognitive and behavioral goals may be practiced without these specific details. For example, for conciseness and clarity selected aspects have been shown in block diagram form rather than in detail. Some portions of the detailed descriptions provided herein may be presented in terms of instructions that operate on data that is stored in a computer memory. Such descriptions and representations are used by those skilled in the art to describe and convey the substance of their work to others skilled in the art. In general, an algorithm refers to a self-consistent sequence of steps leading to a desired result, where a "step" refers to a manipulation of physical quantities which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities.

Unless specifically stated otherwise as apparent from the foregoing discussion, it is appreciated that, throughout the foregoing description, discussions using terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

It is worthy to note that any reference to "one aspect" or "an aspect" means that a particular feature, structure, or characteristic described in connection with the aspect is included in at least one aspect. Thus, appearances of the phrases "in one aspect" or "in an aspect" in various places throughout the specification are not necessarily all referring to the same aspect. Furthermore, the particular features, structures or characteristics may be combined in any suitable manner in one or more aspects.

Although various aspects have been described herein, many modifications, variations, substitutions, changes, and equivalents to those aspects may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed aspects. The following claims are intended to cover all such modification and variations.

Some or all of the aspects described herein may generally comprise technologies for system and method for noninvasive identification of cognitive and behavioral goals, or otherwise according to technologies described herein. In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The foregoing detailed description has set forth various aspects of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one aspect, several portions of the subject matter described herein may be implemented via Application Specific Integrated Circuits (ASICs), Field Programmable Gate Arrays (FPGAs), digital signal processors (DSPs), or other integrated formats. Those skilled in the art will recognize, however, that some aspects disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative aspect of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

All of the above-mentioned U.S. patents, U.S. patent application publications, U.S. patent applications, foreign patents, foreign patent applications, non-patent publications referred to in this specification and/or listed in any Application Data Sheet, or any other disclosure material are incorporated herein by reference, to the extent not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

Although various aspects have been described herein, many modifications, variations, substitutions, changes, and equivalents to those aspects may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed aspects. The following claims are intended to cover all such modification and variations.

In summary, numerous benefits have been described which result from employing the concepts described herein. The foregoing description of the one or more aspects has been presented for purposes of illustration and description. It is not intended to be exhaustive or limiting to the precise form disclosed. Modifications or variations are possible in light of the above teachings. The one or more aspects were chosen and described in order to illustrate principles and practical application to thereby enable one of ordinary skill in the art to utilize the various aspects and with various modifications as are suited to the particular use contemplated. It is intended that the claims submitted herewith define the overall scope.

Various aspects of the present disclosure may be describedin accordance with one or more of the following examples.

Example 1. A brain machine interface system for use with an electroencephalogram to identify a behavioral intent of a person, the system comprising: an electroencephalogram configured to sense electromagnetic signals generated by a brain of a person, wherein the electromagnetic signals comprise a time component and a frequency component; a monitor configured to monitor a response of the person to a stimulus and a characteristic of the stimulus; a synchronization module configured to synchronize the sensed electromagnetic signals with the response and the characteristic to determine a set of electromagnetic signals corresponding to the monitored response of the person and the characteristic; a processor configured to process the set of electromagnetic signals and to extract feature vectors, wherein each of the feature vectors define a class of behavioral intent; and wherein the processor is further configured to determine the behavioral intent of the person based on the feature vectors.

Example 2. The brain machine interface system of Example 1, wherein the monitor is an eye tracking monitor to determine that the person is looking at a visual stimulus.

Example 3. The brain machine interface system of Example 1 or Example 2, wherein the monitor is an auditory monitor to determine the presence of an auditory stimulus based on an auditory volume corresponding to the auditory stimulus.

Example 4. The brain machine interface system of one or more of Example 1 through Example 3, further comprising: a simulation interface configured to display the stimulus.

Example 5. The brain machine interface system of one or more of Example 1 through Example 4, further comprising: a context classification module configured to classify a context of the electromagnetic signals, wherein the context is one of an auditory or a visual context; a behavioral intent classification module to classify the feature vectors.

Example 6. The brain machine interface system of one or more of Example 1 through Example 5, further comprising: a prosthetic limb configured to perform an action based on machine executable instructions executed by the processor, wherein the machine executable instructions correspond to the determined behavioral intent.

Example 7. The brain machine interface system of one or more of Example 1 through Example 6, further comprising: a sensor configured to sense biometric and motion sensor data corresponding to the person, wherein the processor is further configured to generate feedback based on the biometric and the motion sensor data.

Example 8. A brain machine interface comprising: an electroencephalogram configured to sense electromagnetic signals generated by a brain of a person, wherein the electromagnetic signals comprise a time component and a frequency component; an eye tracking monitor configured to determine that the person is looking at a first stimulus; an auditory monitor configured to determine the presence of a second stimulus based on an auditory volume corresponding to the second stimulus; a processor configured to segment the electromagnetic signals into a first segment and a second segment, wherein the first segment corresponds to the first stimulus and the second segment corresponds to the second stimulus; wherein the processor is configured to process the first segment and the second segment and wherein the processor is configured to: extract a first set of feature vectors from the first segment and a second set of feature vectors from the second segment, wherein each of the first set and the second set of feature vectors define a class of behavioral intent; and determine a first behavioral intent based on the first set of feature vectors and a second behavioral intent based on the second set of feature vectors.

Example 9. The brain machine interface of Example 8, wherein the first stimulus is one of a threat stimulus, friendly stimulus, or a neutral stimulus.

Example 10. The brain machine interface of Example 9, wherein the first behavioral intent is one of engage a threat stimulus, communicate with a friendly stimulus, ignore a neutral stimulus.

Example 11. The brain machine interface of one or more of Example 8 through Example 10, wherein the second stimulus is one of a near range stimulus, a mid range stimulus, and a far range stimulus.

Example 12. The brain machine interface of Example 11, wherein the second behavioral intent is one of slew a gunner, launch an unmanned aerial vehicle, alert a team.

Example 13. The brain machine interface of one or more of Example 8 through Example 12, wherein the processing further comprises applying a wavelet transformation to the electric signals to determine that a first frequency and a second frequency are present in a first frequency band.

Example 14. The brain machine interface of Example 13, wherein the first frequency is in a delta frequency band and the second frequency is one of a beta and a gamma frequency band.

Example 15. A method for identifying a behavioral intent of a person, the method comprising: sensing, by an electroencephalogram attached to a person, electromagnetic signals generated by a brain of the person, wherein the electromagnetic signals comprise a time component and a frequency component; detecting, by a monitor, an eye movement of the person and a volume of an auditory stimulus, wherein the eye movement corresponds to a visual stimulus; extracting, by a processor, a first set of feature vectors corresponding to the visual stimulus and a second set of feature vectors corresponding to the auditory stimulus, wherein each of the feature vectors define a class of behavioral intent; and determining, by the processor, a behavioral intent of the person based on the first set of feature vectors and the second set of feature vectors.

Example 16. The method of Example 15, further comprising: synchronizing the electromagnetic signals with the visual stimulus and the auditory stimulus.

Example 17. The method of Example 15 or Example 16, further comprising: pre-processing, by the processor, the electromagnetic signals, wherein the pre-processing comprises filtering and referencing the electromagnetic signals; and extracting, by the processor, spectral features from the electromagnetic signals.

Example 18. The method of Example 17, further comprising: determining, by the processor, a first frequency band and a second frequency band of the spectral features.

Example 19. The method of Example 18, further comprising: applying, by the processor, a wavelet transformation to the electromagnetic signals, wherein the wavelet transformation is applied over a period of time corresponding to the time component; determining a bicoherence element to define a measure of phase coupling based on the first frequency band and the second frequency band, wherein the measure of phase coupling corresponds to the first set and the second set of the feature vectors.

Example 20. The method of Example 19, further comprising: extracting the first set and the second set of feature vectors based on the measure of phase coupling.

Example 21. A system for noninvasive identification of cognitive and behavioral goals as shown and described.

Example 22. A method for noninvasive identification of cognitive and behavioral goals substantially as shown and described.

Example 23. A system for noninvasive identification of cognitive and behavioral goals, the system comprising: a simulated interface; an EEG monitor to detect EEG waves; an eye tracking monitor to detect eye movement; an auditory monitor to receive auditory events; a synchronization task configured to synchronize the EEG, eye movement, and simulation data; a pre-processor task to pre-process the EEG data; a feature extraction task to extract EEG features from the EEG data; a context classification task to classify the context of the extracted EEG features; a goal classification task to classify the goal; and a feedback task to provide feedback to simulated interface.

Example 24. A method for noninvasive identification of cognitive and behavioral goals, the system comprising: simulating an interface; detecting EEG waves and storing EEG data; detecting eye movement and storing eye movement data; receiving and storing auditory events; synchronizing the EEG, eye movement, and simulation data; pre-processing the EEG data; extracting EEG features from the EEG data; classifying the context of the extracted EEG features; classifying a goal; and providing feedback to the simulated interface.

The invention claimed is:

1. A brain machine interface system for use with an electroencephalogram to identify a behavioral intent of a person, the system comprising:
   an electroencephalogram configured to sense electromagnetic signals generated by a brain of a person, wherein the electromagnetic signals comprise a time component and a frequency component;
   a physiological sensor configured to monitor a response of the person to a stimulus and a characteristic of the stimulus;
   a synchronization module configured to synchronize the sensed electromagnetic signals with the response and the characteristic to determine a set of electromagnetic signals corresponding to the monitored response of the person and the characteristic; and
   a processor configured to process the set of electromagnetic signals and to extract feature vectors, wherein the processor is configured to:
      extract spectral features from the electromagnetic signals;
      determine a first frequency band and a second frequency band of the spectral features; and
      determine a bicoherence element to define a measure of phase coupling based on the first frequency band and the second frequency band, wherein the measure of phase coupling corresponds to a first set of feature vectors and a second set of feature vectors derived from the at least one stimulus,
      wherein each of the feature vectors define a class of behavioral intent; and
   a prosthetic limb configured to perform an action based on machine executable instructions executed by the processor,
   wherein the processor is further configured to determine the behavioral intent of the person based on the feature vectors,
   wherein the machine executable instructions, executed by the processor, correspond to the determined behavioral intent, and
   wherein the prosthetic limb is configured to receive motion instructions from the processor and to move according to the behavioral intent of the person.

2. The brain machine interface system of claim 1, wherein the monitor physiological sensor is an eye tracking monitor configured to determine that the person is looking at a visual stimulus.

3. The brain machine interface system of claim 2, further comprising:
   a camera system configured for use by a machine vision module, wherein the machine vision module is configured to determine a trajectory of the prosthetic limb to a position of a target.

4. The brain machine interface system of claim 3, wherein the visual stimulus comprises the target and the behavioral intent of the person is determined at least in part by data received by the processor from the eye tracking monitor.

5. The brain machine interface system of claim 1, further comprising:
   a context classification module configured to classify a context of the electromagnetic signals, wherein the context is a visual context; and
   a behavioral intent classification module to classify the feature vectors.

6. The brain machine interface system of claim 1, further comprising:
   a sensor configured to sense biometric and motion sensor data corresponding to the person, wherein the processor is further configured to generate feedback based on the biometric and the motion sensor data.

7. The brain machine interface system of claim 1, wherein the behavioral intent comprises causing the prosthetic limb to mimic a function of a natural limb.

8. The brain machine interface system of claim 7, wherein the natural limb comprises a natural arm and hand, and the behavioral intent comprises mimicking a function of the natural limb to pick up an object.

9. The brain machine interface system of claim 1, wherein the processing further comprises applying a wavelet transformation to the electromagnetic signals to determine that a first frequency and a second frequency are present in a first frequency band.

10. A method of operating a prosthetic limb by a person, the method comprising:
   sensing, by an electroencephalogram, a plurality of electromagnetic signals generated by a brain of the person, wherein the electromagnetic signals comprise a time component and a frequency component;
   monitoring, by a physiological sensor, a response of the person to a stimulus and a characteristic of the stimulus;
   synchronizing, by a synchronization module, the sensed electromagnetic signals with the response and the characteristic to determine a set of electromagnetic signals corresponding to the monitored response of the person and the characteristic;
   extracting, by a processor, a plurality of spectral features from the electromagnetic signals;
   determining, by the processor, a first frequency band and a second frequency band of the plurality of spectral features; and
   determining, by the processor, a bicoherence element to define a measure of phase coupling based on the first frequency band and the second frequency band, wherein the measure of phase coupling corresponds to a first set of feature vectors and a second set of feature vectors derived from the at least one stimulus, and wherein each of the feature vectors define a class of behavioral intent;

determining, by the processor, a behavioral intent of the person based on the feature vectors, wherein the behavioral intent comprises a targeted motion of the prosthetic limb;

executing, by the processor, machine executable instructions that correspond to the behavioral intent, transmitting, by the processor to the prosthetic limb, motion instructions corresponding to the behavioral intent, and moving, by the prosthetic limb, according to the behavioral intent.

11. The method of claim 10, further comprising:

receiving, by a machine vision module, imaging data from a camera, wherein the imaging data comprise an image of a target object and the prosthetic limb.

12. The method of claim 11, further comprising:

determining, by the machine vision module, a location of the prosthetic limb in relation to the target object based on the imaging data from the camera.

13. The method of claim 12, further comprising:

determining, by the processor, a trajectory of the prosthetic limb to the target object based on the imaging data from the machine vision module.

14. The method of claim 13, wherein monitoring, by monitor a physiological sensor, a response of the person to a stimulus comprises monitoring, by an eye tracking monitor that the person is looking at the target object.

15. The method of claim 13, wherein determining, by the processor, a behavioral intent of the person based on the feature vectors further comprises:

determining, by the processor, the behavior intent of the person based on eye tracking data received from the eye tracking monitor.

* * * * *